United States Patent
McCaffrey et al.

(10) Patent No.: US 11,185,244 B2
(45) Date of Patent: Nov. 30, 2021

(54) FFR CATHETER WITH SUSPENDED PRESSURE SENSOR

(71) Applicant: Medtronic Vascular, Inc., Santa Rosa, CA (US)

(72) Inventors: Gerry McCaffrey, Tuam (IE); Theresa Wittrock, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 453 days.

(21) Appl. No.: 16/102,459

(22) Filed: Aug. 13, 2018

(65) Prior Publication Data
US 2020/0046230 A1   Feb. 13, 2020

(51) Int. Cl.
| | |
|---|---|
| *A61B 5/02* | (2006.01) |
| *A61B 5/026* | (2006.01) |
| *A61B 5/0215* | (2006.01) |
| *A61M 25/09* | (2006.01) |
| *A61B 5/00* | (2006.01) |
| *A61M 25/01* | (2006.01) |

(52) U.S. Cl.
CPC .......... *A61B 5/026* (2013.01); *A61B 5/02007* (2013.01); *A61B 5/0215* (2013.01); *A61M 25/09* (2013.01); *A61B 5/6852* (2013.01); *A61B 2562/0247* (2013.01); *A61B 2562/12* (2013.01); *A61M 2025/0177* (2013.01)

(58) Field of Classification Search
CPC ... A61B 5/026; A61B 5/02007; A61B 5/0215; A61B 5/6852; A61B 2562/0247; A61B 2562/12; A61B 5/6851; A61M 25/09; A61M 2025/0177
See application file for complete search history.

(56) References Cited

U.S. PATENT DOCUMENTS

| | | |
|---|---|---|
| 4,718,425 A | 1/1988 | Tanaka et al. |
| 4,771,782 A | 9/1988 | Millar |
| 4,796,641 A | 1/1989 | Mills et al. |
| 4,815,472 A | 3/1989 | Wise et al. |
| 4,850,358 A | 7/1989 | Millar |
| 4,901,731 A | 2/1990 | Millar |
| 4,924,877 A | 5/1990 | Brooks |
| 4,928,693 A | 5/1990 | Goodin et al. |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |

(Continued)

FOREIGN PATENT DOCUMENTS

| | | |
|---|---|---|
| DE | 102008045878 | 3/2010 |
| EP | 0263190 | 10/1986 |

(Continued)

OTHER PUBLICATIONS

PCT/US2019/045527, International Search Report, dated Jan. 13, 2020.

*Primary Examiner* — Andrey Shostak

(57) ABSTRACT

A catheter for measuring a pressure distal of a stenosis includes a shaft including a housing in a distal portion of the shaft. A flexible printed circuit board is coupled to the housing. A pressure sensor is coupled to the flexible printed circuit board and is suspended within the housing. An aperture enables blood flow into the housing and into contact with the pressure sensor.

15 Claims, 15 Drawing Sheets

(56) References Cited

U.S. PATENT DOCUMENTS

| | | |
|---|---|---|
| 5,029,585 A | 7/1991 | Lieber et al. |
| 5,046,497 A | 9/1991 | Millar |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A | 1/1997 | Shoup et al. |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A | 2/1998 | Corl et al. |
| 5,813,997 A | 9/1998 | Imran et al. |
| 5,827,243 A | 10/1998 | Palestrant |
| 5,873,835 A | 2/1999 | Hastings et al. |
| 5,902,248 A | 5/1999 | Millar et al. |
| 5,964,714 A | 10/1999 | Lafontaine |
| 6,033,366 A | 3/2000 | Brockway et al. |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,179,856 B1 | 1/2001 | Barbere |
| 6,182,513 B1 | 2/2001 | Stemme et al. |
| 6,193,669 B1 | 2/2001 | Degany et al. |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 11/2001 | Hoek et al. |
| 6,336,906 B1 | 1/2002 | Hammarstrom et al. |
| 6,354,999 B1 | 3/2002 | Dgany et al. |
| 6,379,308 B1 | 4/2002 | Brockway et al. |
| 6,394,986 B1 | 5/2002 | Millar |
| 6,409,677 B1 | 6/2002 | Tulkki |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,667 B2 | 9/2003 | Smith |
| 6,659,957 B1 | 12/2003 | Vardi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B1 | 5/2004 | Atsumi |
| 6,754,608 B2 | 6/2004 | Svanerudh et al. |
| 6,767,327 B1 | 7/2004 | Corl et al. |
| 6,821,287 B1 | 11/2004 | Jang |
| 6,860,851 B2 | 3/2005 | Knudson et al. |
| 6,868,736 B2 | 3/2005 | Sawatari et al. |
| 6,926,674 B2 | 8/2005 | Tenerz et al. |
| 6,938,474 B2 | 9/2005 | Melvangs |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway et al. |
| 7,060,038 B2 | 6/2006 | Letort et al. |
| 7,097,620 B2 | 8/2006 | Corl et al. |
| 7,112,170 B2 | 9/2006 | Schock et al. |
| 7,134,994 B2 | 11/2006 | Alpert et al. |
| 7,137,953 B2 | 11/2006 | Eigler et al. |
| 7,211,048 B1 | 5/2007 | Najafi et al. |
| 7,222,539 B2 | 5/2007 | Tulkki |
| 7,229,403 B2 | 6/2007 | Schock et al. |
| 7,245,789 B2 | 7/2007 | Bates. et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B1 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway et al. |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,837,650 B1 | 11/2010 | Cox et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson et al. |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson et al. |
| 8,419,647 B2 | 4/2013 | Corl et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |

(56) References Cited

U.S. PATENT DOCUMENTS

| | | | |
|---|---|---|---|
| 9,186,072 | B2 | 11/2015 | Manstrom et al. |
| 9,220,461 | B2 | 12/2015 | Samuelsson et al. |
| 9,259,161 | B2 | 2/2016 | Suchecki et al. |
| 9,289,137 | B2 | 3/2016 | Corl |
| 9,314,584 | B1 | 4/2016 | Riley et al. |
| 9,332,916 | B2 | 5/2016 | Kassab |
| 9,339,348 | B2 | 5/2016 | Davies et al. |
| 2001/0051769 | A1 | 12/2001 | Hoek et al. |
| 2002/0013527 | A1 | 1/2002 | Hoek et al. |
| 2002/0035331 | A1 | 3/2002 | Brockway et al. |
| 2002/0059827 | A1 | 5/2002 | Smith |
| 2002/0065472 | A1 | 5/2002 | Brockway et al. |
| 2002/0072880 | A1 | 6/2002 | Svanerudh et al. |
| 2002/0157473 | A1 | 10/2002 | Stemme et al. |
| 2002/0173724 | A1 | 11/2002 | Dorando et al. |
| 2003/0018273 | A1 | 1/2003 | Corl et al. |
| 2003/0032886 | A1 | 2/2003 | Dgany et al. |
| 2003/0033095 | A1 | 2/2003 | Svanerudh et al. |
| 2003/0040674 | A1 | 2/2003 | Corl et al. |
| 2003/0159518 | A1 | 8/2003 | Sawatari et al. |
| 2003/0163052 | A1 | 8/2003 | Mott et al. |
| 2003/0176850 | A1 | 9/2003 | Melvas |
| 2003/0195428 | A1 | 10/2003 | Brockway et al. |
| 2003/0216621 | A1 | 11/2003 | Alpert et al. |
| 2004/0067000 | A1 | 4/2004 | Bates et al. |
| 2004/0082844 | A1 | 4/2004 | Vardi et al. |
| 2004/0082866 | A1 | 4/2004 | Mott et al. |
| 2004/0116816 | A1 | 6/2004 | Tenerz et al. |
| 2004/0143240 | A1 | 7/2004 | Armstrong et al. |
| 2004/0143261 | A1 | 7/2004 | Hartley et al. |
| 2004/0157790 | A1 | 8/2004 | Herweijer et al. |
| 2004/0162548 | A1 | 8/2004 | Reiser |
| 2004/0167385 | A1 | 8/2004 | Rioux et al. |
| 2004/0176790 | A1 | 9/2004 | Coyle |
| 2004/0230131 | A1 | 11/2004 | Kassab et al. |
| 2004/0254442 | A1 | 12/2004 | Williams et al. |
| 2005/0000294 | A1 | 1/2005 | Tenerz et al. |
| 2005/0011272 | A1 | 1/2005 | Tenerz |
| 2005/0043670 | A1 | 2/2005 | Rosenberg |
| 2005/0049451 | A1 | 3/2005 | Schock et al. |
| 2005/0054905 | A1* | 3/2005 | Corl .................. A61B 5/14539 600/309 |
| 2005/0187487 | A1 | 8/2005 | Azizkhan et al. |
| 2005/0268724 | A1 | 12/2005 | Tenerz |
| 2005/0268725 | A1 | 12/2005 | Tulkki |
| 2006/0052700 | A1 | 3/2006 | Svanerudh |
| 2006/0074318 | A1 | 4/2006 | Ahmed et al. |
| 2006/0094966 | A1 | 5/2006 | Brockway et al. |
| 2006/0094982 | A1 | 5/2006 | Corl et al. |
| 2006/0142756 | A1 | 6/2006 | Davies et al. |
| 2006/0207335 | A1 | 9/2006 | Tenerz et al. |
| 2006/0241505 | A1 | 10/2006 | Ahmed et al. |
| 2006/0287569 | A1 | 12/2006 | Schock et al. |
| 2007/0060820 | A1 | 3/2007 | Lofgren et al. |
| 2007/0060822 | A1 | 3/2007 | Alpert et al. |
| 2007/0078352 | A1 | 4/2007 | Pijls |
| 2007/0106142 | A1 | 5/2007 | Von Malmborg et al. |
| 2007/0106165 | A1 | 5/2007 | Tulkki |
| 2007/0116408 | A1 | 5/2007 | Eberle et al. |
| 2007/0133925 | A1 | 6/2007 | Bates et al. |
| 2007/0135718 | A1 | 6/2007 | Corl et al. |
| 2007/0191717 | A1 | 8/2007 | Rosen et al. |
| 2007/0220986 | A1 | 9/2007 | Smith et al. |
| 2007/0255144 | A1 | 11/2007 | Tulkki et al. |
| 2007/0255145 | A1 | 11/2007 | Smith et al. |
| 2008/0077085 | A1 | 3/2008 | Eidenschink |
| 2008/0119739 | A1 | 5/2008 | Vardi et al. |
| 2008/0119758 | A1 | 5/2008 | Samuelsson et al. |
| 2008/0132806 | A1 | 6/2008 | Smith |
| 2008/0139897 | A1 | 6/2008 | Ainsworth et al. |
| 2008/0146993 | A1 | 6/2008 | Krishna |
| 2008/0200770 | A1 | 8/2008 | Hubinette |
| 2008/0255471 | A1 | 10/2008 | Naghavi et al. |
| 2008/0262470 | A1 | 10/2008 | Lee et al. |
| 2008/0269572 | A1 | 10/2008 | Kanz et al. |
| 2009/0059727 | A1 | 3/2009 | Bates et al. |
| 2009/0082678 | A1 | 3/2009 | Smith |
| 2009/0088609 | A1 | 4/2009 | Schmitz-Rode et al. |
| 2009/0088650 | A1 | 4/2009 | Corl |
| 2009/0124880 | A1 | 5/2009 | Smith |
| 2009/0125007 | A1 | 5/2009 | Splinter |
| 2009/0248049 | A1 | 10/2009 | Perkins |
| 2009/0281394 | A1 | 11/2009 | Russell et al. |
| 2010/0014810 | A1 | 1/2010 | Eberle et al. |
| 2010/0087732 | A1 | 4/2010 | Eberle et al. |
| 2010/0109104 | A1 | 5/2010 | Tiensuu et al. |
| 2010/0113942 | A1 | 5/2010 | Eberle |
| 2010/0135111 | A1 | 6/2010 | Bates et al. |
| 2010/0152607 | A1 | 6/2010 | Kassab |
| 2010/0234698 | A1 | 9/2010 | Manstrom et al. |
| 2010/0241008 | A1 | 9/2010 | Belleville et al. |
| 2010/0280330 | A1 | 11/2010 | Samuelsson et al. |
| 2010/0286536 | A1 | 11/2010 | Samuelsson et al. |
| 2010/0286537 | A1 | 11/2010 | Pijls |
| 2011/0004198 | A1 | 1/2011 | Hoch |
| 2011/0060229 | A1 | 3/2011 | Hulvershorn et al. |
| 2011/0066047 | A1 | 3/2011 | Belleville et al. |
| 2011/0071407 | A1 | 3/2011 | Hubinette et al. |
| 2011/0083521 | A1 | 4/2011 | Hollander et al. |
| 2011/0123154 | A1 | 5/2011 | Eberle et al. |
| 2011/0137140 | A1 | 6/2011 | Tearney et al. |
| 2011/0178383 | A1 | 7/2011 | Kassab |
| 2011/0178413 | A1 | 7/2011 | Schmitt et al. |
| 2011/0178417 | A1 | 7/2011 | Kassab |
| 2011/0196255 | A1 | 8/2011 | Kassab |
| 2011/0245693 | A1 | 10/2011 | Hastings et al. |
| 2011/0251497 | A1 | 10/2011 | Corl et al. |
| 2011/0306867 | A1 | 12/2011 | Gopinathan et al. |
| 2011/0319773 | A1 | 12/2011 | Kanz et al. |
| 2012/0053918 | A1 | 3/2012 | Taylor |
| 2012/0071782 | A1 | 3/2012 | Patil et al. |
| 2012/0072190 | A1 | 3/2012 | Sharma et al. |
| 2012/0101355 | A1 | 4/2012 | Gopinathan et al. |
| 2012/0101369 | A1 | 4/2012 | Patil et al. |
| 2012/0108943 | A1 | 5/2012 | Bates et al. |
| 2012/0136244 | A1 | 5/2012 | Manstrom et al. |
| 2012/0172731 | A1 | 7/2012 | Smith |
| 2012/0172732 | A1 | 7/2012 | Meyer |
| 2012/0203118 | A1 | 8/2012 | Samuelsson et al. |
| 2012/0220836 | A1 | 8/2012 | Alpert et al. |
| 2012/0220837 | A1 | 8/2012 | Alpert et al. |
| 2012/0220883 | A1 | 8/2012 | Manstrom et al. |
| 2012/0227505 | A1 | 9/2012 | Belleville et al. |
| 2012/0271178 | A1 | 10/2012 | Smith |
| 2012/0278008 | A1 | 11/2012 | Davies et al. |
| 2012/0316419 | A1 | 12/2012 | Chevalier |
| 2013/0015975 | A1 | 1/2013 | Huennekens et al. |
| 2013/0023762 | A1 | 1/2013 | Huennekens et al. |
| 2013/0023763 | A1 | 1/2013 | Huennekens et al. |
| 2013/0046190 | A1 | 2/2013 | Davies |
| 2013/0060133 | A1 | 3/2013 | Kassab et al. |
| 2013/0090555 | A1 | 4/2013 | Kassab |
| 2013/0096409 | A1 | 4/2013 | Hiltner et al. |
| 2013/0109980 | A1 | 5/2013 | Teo |
| 2013/0116579 | A1 | 5/2013 | Svanerudh |
| 2013/0131523 | A1 | 5/2013 | Suchecki et al. |
| 2013/0190633 | A1 | 7/2013 | Dorando et al. |
| 2013/0216481 | A1 | 8/2013 | Rosenmeier |
| 2013/0303914 | A1 | 11/2013 | Hiltner et al. |
| 2013/0324864 | A1 | 12/2013 | Manstrom et al. |
| 2014/0024235 | A1 | 1/2014 | Russell |
| 2014/0024950 | A1 | 1/2014 | Hiltner et al. |
| 2014/0086461 | A1 | 3/2014 | Yao et al. |
| 2014/0180140 | A1 | 6/2014 | Alpert |
| 2014/0180141 | A1 | 6/2014 | Millett |
| 2014/0187980 | A1 | 7/2014 | Burkett |
| 2014/0187984 | A1 | 7/2014 | Burkett |
| 2014/0276142 | A1 | 9/2014 | Dorando |
| 2014/0379269 | A1 | 12/2014 | Schmitt |
| 2015/0032011 | A1 | 1/2015 | McGowan et al. |
| 2015/0074995 | A1 | 3/2015 | Patil et al. |
| 2015/0105673 | A1 | 4/2015 | Gregorich |
| 2015/0112191 | A1 | 4/2015 | Gilboa et al. |
| 2015/0141853 | A1 | 5/2015 | Miller et al. |

(56) References Cited

U.S. PATENT DOCUMENTS

| | | |
|---|---|---|
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0223707 A1 | 8/2015 | Ludoph |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2016/0022153 A1 | 1/2016 | Dorando |
| 2016/0066802 A1 | 3/2016 | Keller |
| 2016/0081564 A1 * | 3/2016 | McCaffrey ............ A61B 5/6852 600/486 |
| 2016/0106321 A1 | 4/2016 | Sharma et al. |
| 2018/0093078 A1 * | 4/2018 | Patil .................... A61B 5/6851 |

FOREIGN PATENT DOCUMENTS

| | | | |
|---|---|---|---|
| EP | 1419796 | 5/2004 | |
| EP | 1702641 | 9/2006 | |
| EP | 3209199 A2 | 8/2017 | |
| JP | 10-33488 | 10/1998 | |
| JP | 2004-194996 | 7/2004 | |
| JP | 10-137199 | 5/2010 | |
| WO | WO2003/022122 | 3/2003 | |
| WO | WO2011/120565 | 10/2011 | |
| WO | WO2011/161212 | 12/2011 | |
| WO | WO2012/093260 | 7/2012 | |
| WO | WO2012/173697 | 12/2012 | |
| WO | WO2013/061281 | 5/2013 | |
| WO | WO2014/176448 | 10/2014 | |
| WO | WO2015/150128 | 10/2015 | |
| WO | 2015195023 A1 | 12/2015 | |
| WO | WO-2015195023 A1 * | 12/2015 | ............. H05K 1/189 |
| WO | WO2016/001017 | 1/2016 | |

* cited by examiner

FFR CATHETER WITH SUSPENDED PRESSURE SENSOR

FIELD OF THE INVENTION

The present invention relates to systems, and methods for manufacturing systems for calculating a Fractional Flow Reserve (FFR). More particularly, the present invention relates to a distal shaft of an FFR device with a pressure sensor coupled to a flexible printed circuit board (PCB) and suspended thereon.

BACKGROUND OF THE INVENTION

The severity of a stenosis or lesion in a blood vessel may be assessed by obtaining proximal and distal pressure measurements relative to the given stenosis and using those measurements for calculating a value of a Fractional Flow Reserve (FFR). FFR is defined as the ratio of a first, or distal pressure $P_d$ measured on the distal side of the stenosis to a second, or proximal pressure $P_a$ measured on the proximal side of the stenosis, usually within the aorta. Conventionally, a sensor is placed on a distal portion of a guidewire or FFR wire to measure the distal pressure $P_d$, while an external pressure transducer is fluidly connected via tubing to a guide catheter to measure the proximal, or aortic (AO) pressure $P_a$. Calculation of the FFR value provides a stenosis specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation.

If an interventional treatment is required, the interventional device, such as a balloon catheter, is tracked over a guidewire to the site of the stenosis. Conventional FFR wires generally are not desired by clinicians to be used as guidewires for such interventional devices. Accordingly, if an intervention treatment is required, the clinician generally removes the FFR wire, inserts a conventional guidewire, and tracks the interventional device to the treatment site over the conventional guidewire.

To address this concern, efforts have been made to utilize catheters (micro-catheters) to take pressure measurements for calculating FFR. Using an FFR catheter with a pressure sensor mounted within a distal portion of the catheter to measure the distal pressure $P_d$, a clinician may use a preferred guidewire for tracking the FFR catheter to the site of the stenosis. If an interventional treatment is required, the guidewire used with the FFR catheter may remain in situ and the interventional device may be tracked over the existing guidewire to the site of the stenosis.

The pressure sensor is a sensitive device that can be affected by external stresses as well as stresses emanating from the pressure sensor itself. More precisely, the FFR catheter experiences stresses and strains, or torsional forces as the FFR catheter is advanced through the tortuous vasculature of a patient. These torsional forces on the FFR catheter may be transferred to the pressure sensor mounted thereon. The transferred torsional forces may deflect the diaphragm of the pressure sensor and may result in errors in the measured distal pressure $P_d$, which in turn will may result in inaccurate FFR calculations. Thus, in order to provide a stable pressure output of the pressure sensor, it is desirable to minimize or eliminate stresses on the pressure sensor.

Additionally, manufacture of a distal portion of the FFR catheter with the pressure sensor mounted therein may be difficult. For example, threading of a sensor wire through the distal shaft portion, mounting of the pressure sensor, and connection of the sensor wire to the pressure sensor in a confined space inside the distal portion during manufacture provides both build and maintenance challenges.

Accordingly, there is a need for systems and methods for the manufacture of reduce inaccurate readings resulting from torsional deflection of a pressure sensor of a distal portion of an FFR catheter or a distal portion of an FFR guidewire.

BRIEF SUMMARY OF THE INVENTION

Embodiments hereof are directed to a catheter for measuring a pressure distal of a stenosis. The catheter includes a shaft including a housing in a distal portion of the shaft. A flexible printed circuit board is coupled to the housing. A pressure sensor is coupled to the flexible printed circuit board and suspended within the housing. An aperture is configured to allow blood flow into the housing and into contact with the pressure sensor. In some embodiments, the flexible printed circuit board is coupled to the housing at a fixation point. In some embodiments, the flexible printed circuit board is coupled to the housing at a plurality of fixation points. In some embodiments a cover coupled to the housing, the cover including a first configuration wherein the cover covers the pressure sensor. In some embodiments, the aperture is formed between an inner surface of the cover and an outer surface of the housing.

In some embodiments, a sensor lumen extends through the shaft of the catheter, and the flexible printed circuit board is disposed in the sensor lumen. In some embodiments, at least one through-hole extends radially through the distal portion of the shaft to the sensor lumen. In some embodiments, the at least one through hole is configured to enable access to couple the flexible printed circuit board to the housing. In some embodiments, the housing includes a guidewire lumen.

In some embodiments, the housing includes an open seat and the pressure sensor is suspended within the open seat. In some embodiments, the catheter includes a sensor lumen extending through the shaft. In some embodiments, the sensor lumen includes a first portion proximal of the open seat and a second portion distal of the open seat. In some embodiments, a first portion of the flexible printed circuit board is disposed in the first portion of the sensor lumen, a second portion of the flexible printed circuit board is disposed in the second portion of the sensor lumen, and a third portion of the flexible printed circuit board with the sensor coupled thereto is suspended in the open seat between the first and second portions of the sensor lumen. In some embodiments, a through-hole extends through the housing to the first portion of the sensor lumen. In some embodiments, the second portion of the sensor lumen is sized and shaped to fit the third portion of the flexible printed circuit board with the pressure sensor coupled thereto within the second portion of the sensor lumen.

Embodiments hereof are also directed to a system for calculating a Fractional Flow Reserve of a stenosis in a blood vessel. The system includes a catheter including a shaft with a housing in a distal portion of the shaft. A distal pressure sensor is suspended within the housing. An aperture is configured to provide blood flow to the distal pressure sensor suspended within the housing. The system further includes a proximal pressure-sensing device configured to measure a proximal blood pressure proximal of the stenosis. The system further includes a processing device in communication the distal pressure sensor and the proximal pressure-sensing device. The catheter is configured for placement within a blood vessel such that the housing is distal of the stenosis and blood distal of the stenosis flows through the aperture into the housing and in contact with the distal pressure sensor such that the distal pressure sensor measures a distal blood pressure distal of the stenosis. The processing device is configured to calculate the Fractional Flow Reserve based on the distal blood pressure relative to the proximal blood pressure.

Embodiments hereof are also directed to a system for calculating a Fractional Flow Reserve of a stenosis in a blood vessel. The system includes a guidewire including a housing in a distal portion of the guidewire. A distal pressure sensor is suspended within the housing. An aperture is configured to provide blood flow to the distal pressure sensor suspended within the housing. The system further includes a proximal pressure-sensing device configured to measure a proximal blood pressure proximal of the stenosis. The system further includes a processing device in communication the distal pressure sensor and the proximal pressure-sensing device. The guidewire is configured for placement within a blood vessel such that the housing is distal of the stenosis and blood distal of the stenosis flows through the aperture into the housing and in contact with the distal pressure sensor such that the distal pressure sensor measures a blood pressure distal of the stenosis. The processing device is configured to calculate the Fractional Flow Reserve based on the distal blood pressure relative to the proximal blood pressure.

Embodiments hereof are also directed to a method of manufacturing an FFR catheter. The method includes forming a shaft including a housing in a distal portion of a shaft, a guidewire lumen, and a sensor lumen. The method further includes forming an open seat in the housing. The method further includes coupling a pressure sensor to a flexible printed circuit board and to a sensor trace of the flexible printed circuit board. The method further includes positioning the flexible printed circuit board within the sensor lumen such that the pressure sensor coupled to the flexible printed circuit board is suspended within the open seat of the housing. In some embodiments, the method further includes coupling the flexible printed circuit board to the housing at a fixation point. In some embodiments, the method further includes after the step of positioning the flexible printed circuit board, sliding a cover from a first position proximal or distal of the housing to a second position wherein the cover is positioned over the open seat, and after sliding the cover to the second position, attaching the cover to the housing. In some embodiments, the method further includes forming an aperture in the distal portion of the shaft, wherein the aperture enables blood flow into the open seat with the cover in the second position.

In some embodiments, the sensor lumen includes a first portion proximal of the open seat and a second portion distal of the open seat. In some embodiments, the method includes positioning the flexible printed circuit board such that a first portion of the flexible printed circuit board is in the first portion of the sensor lumen, a second portion of the flexible printed circuit board is in the second portion of the sensor lumen, and a third portion of the flexible printed board with the pressure sensor coupled thereto is distal of the second portion of the sensor lumen. In some embodiments, the method further includes sliding the flexible printed circuit board proximally such that the pressure sensor slides through the second portion of the sensor lumen and into the open seat. In some embodiments, the method further includes coupling the flexible printed circuit board to the housing at a fixation point. In some embodiments, the flexible printed circuit board is coupled to the housing at a first fixation point proximal of the open seat and a second fixation point distal of the open seat.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal" used in the following description to refer to a vessel or a stenosis are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the following detailed description.

Figure 1:
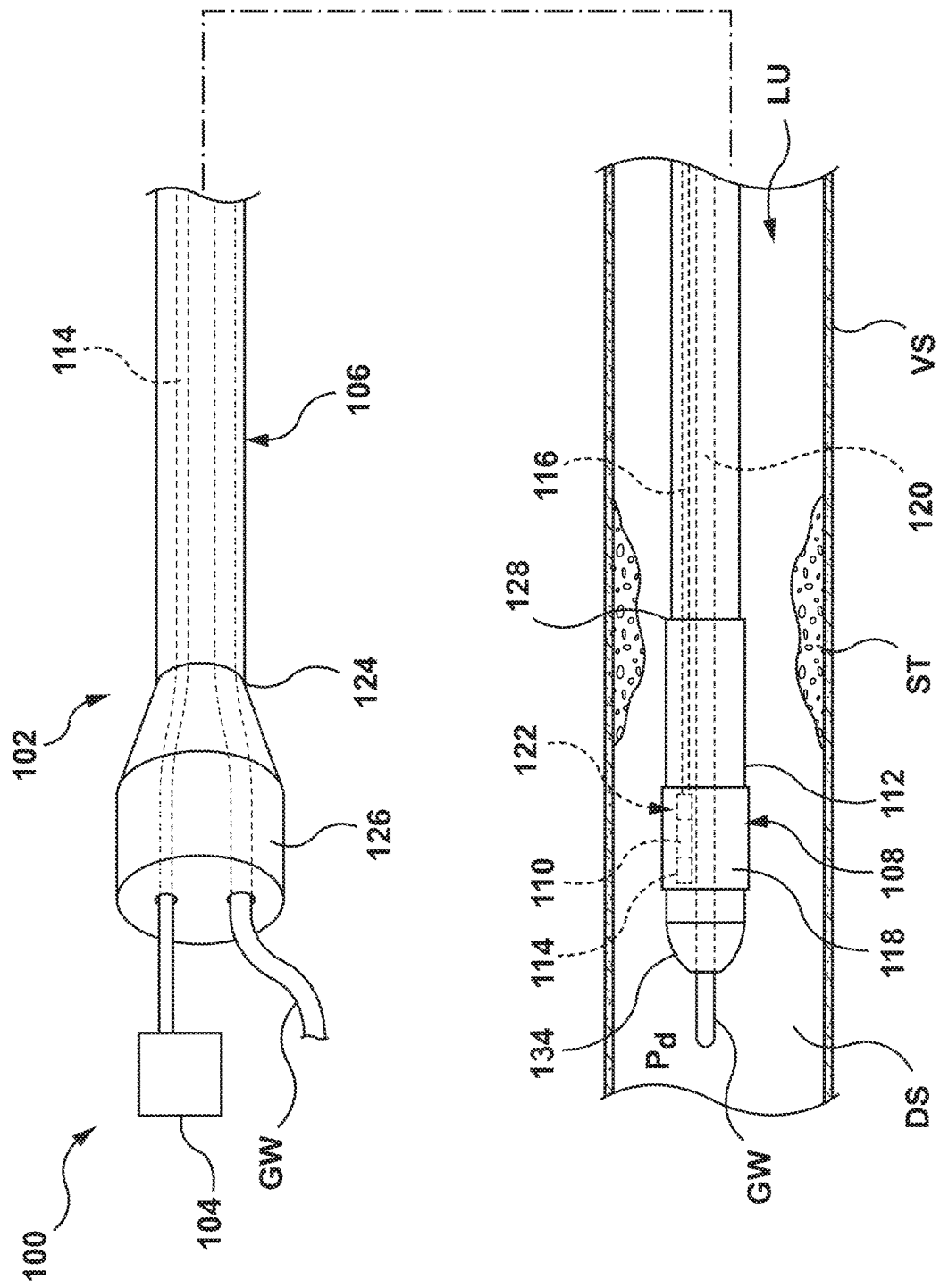
FIG. 1 depicts a partial side and perspective view of a catheter for calculating a Fractional Flow Reserve (FFR) in accordance with an embodiment hereof.

FIG. 1 is a schematic partial side and partial perspective illustration of a system 100 for calculating a Fractional Flow Reserve (FFR) according to an embodiment hereof. The system 100 includes an FFR catheter or FFR micro-catheter 102, a proximal pressure-sensing device (not shown), and a processing device 104. The FFR catheter 102 is configured to be disposed with a proximal portion thereof extending outside of a patient and a distal portion thereof positioned in situ within a lumen LU of a vessel VS having a stenosis ST. In an embodiment, the vessel VS is a blood vessel such as but not limited to a coronary artery. The stenosis ST is generally representative of any blockage or other structural arrangement that results in a restriction to the flow of fluid through the lumen LU of the vessel VS. The stenosis ST may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis ST will depend on the type of vessel being evaluated. In that regard, it is understood that embodiments hereof are applicable to various types of blockages or other narrowing of a vessel that results in decreased fluid flow.

Figure 2:
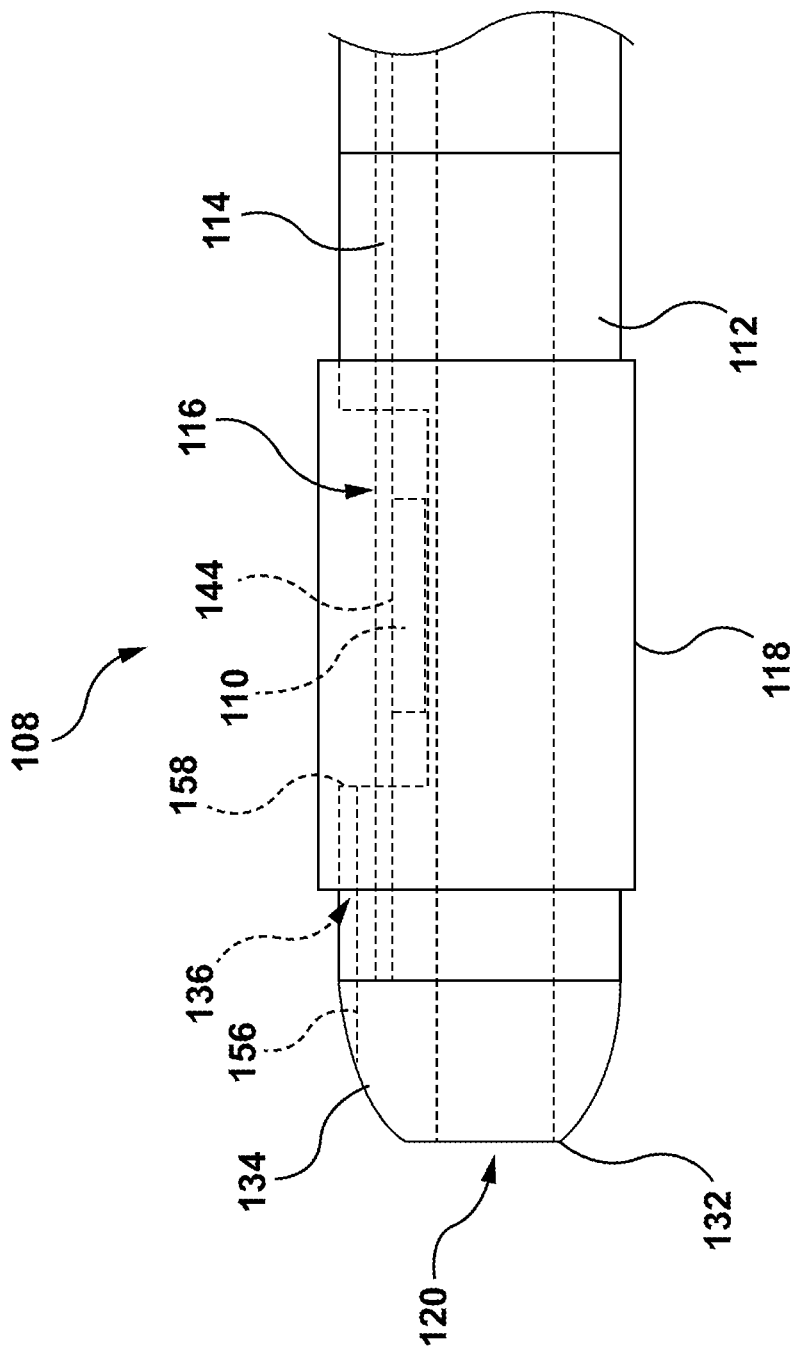
FIG. 2 depicts a longitudinal cross sectional view of a distal portion of the catheter of FIG. 1.
Figure 3:
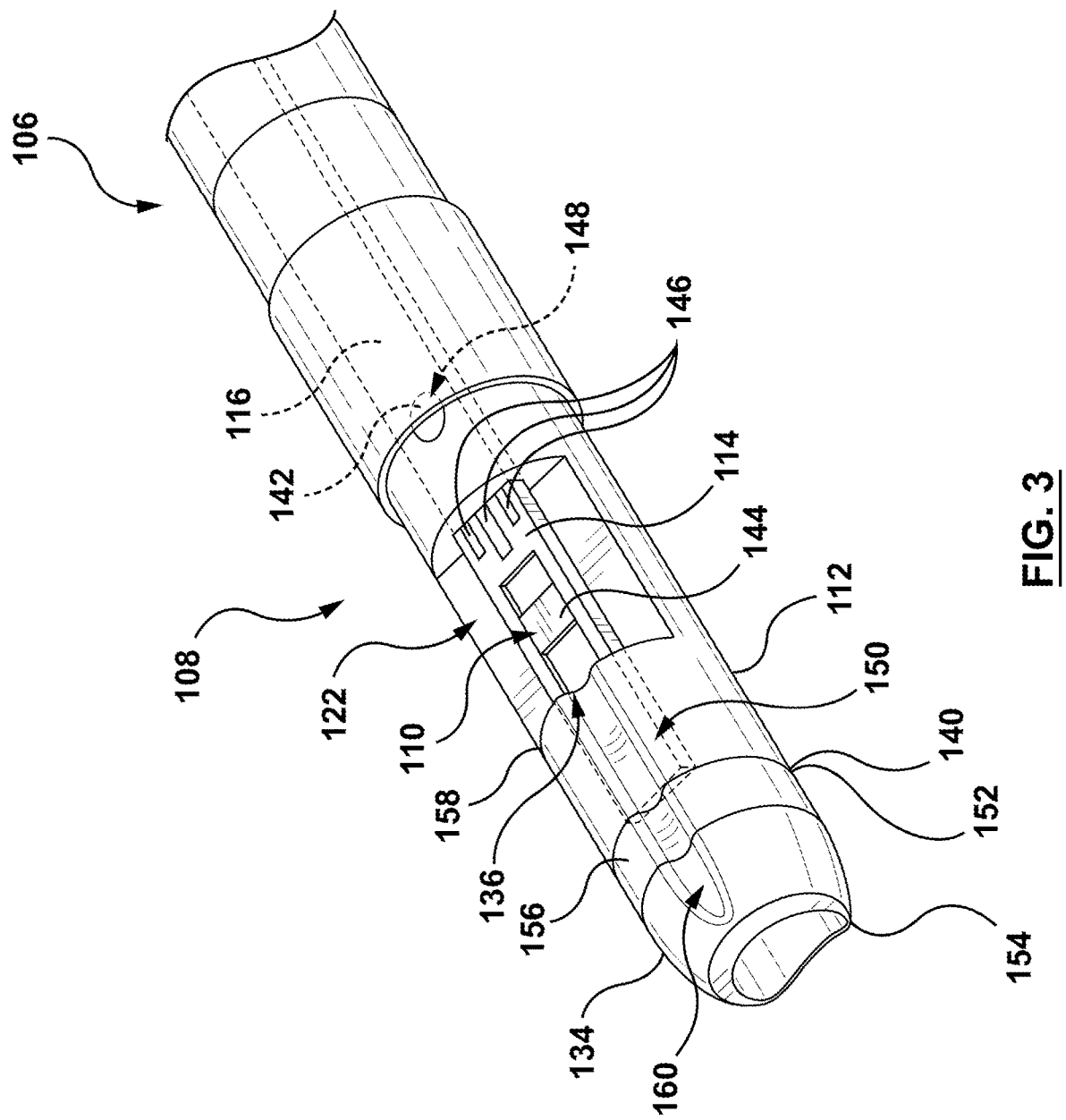
FIG. 3 depicts a perspective illustration of a distal portion of the catheter of FIG. 1 according to an embodiment hereof, with a cover in a second configuration.
Figure 4:
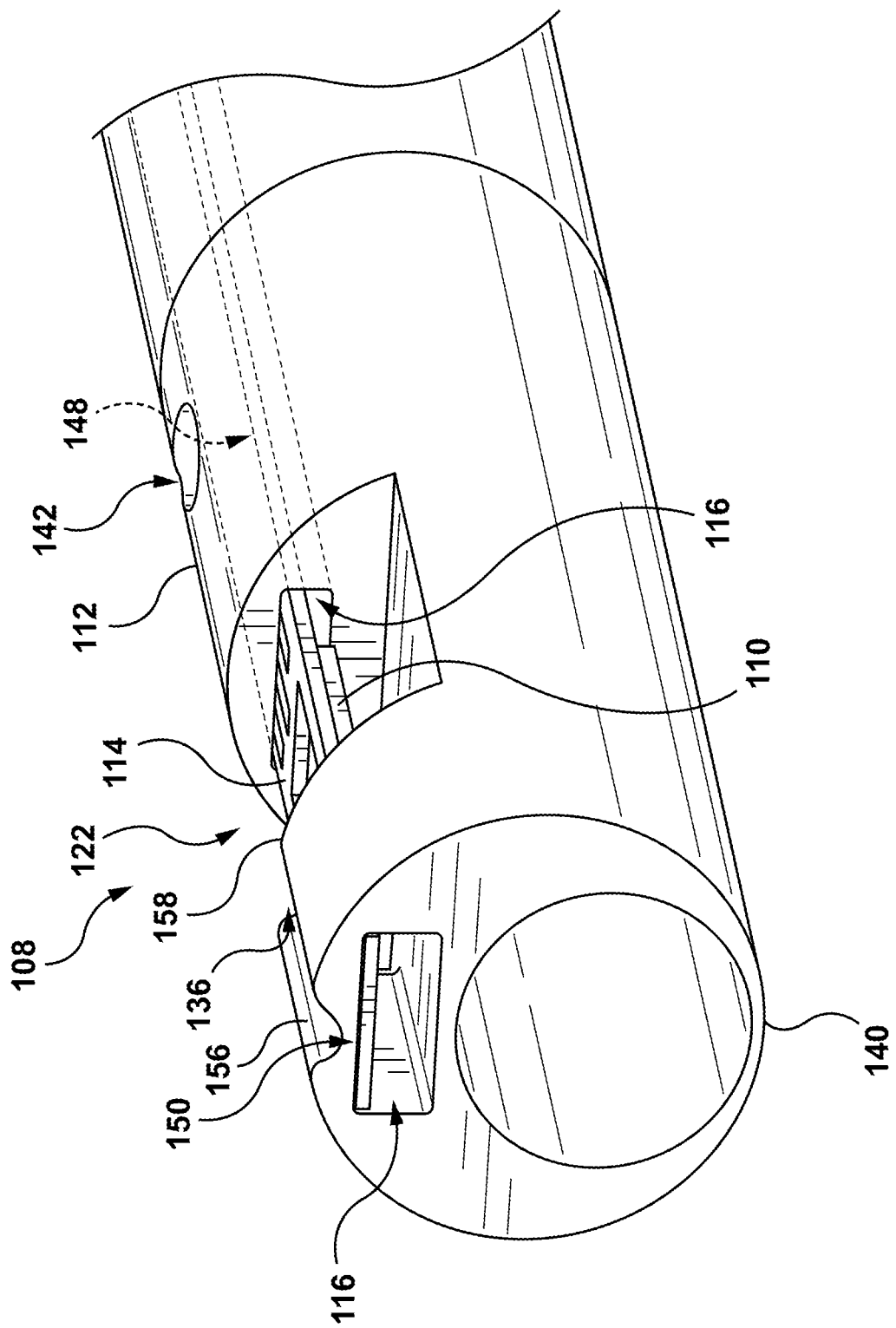
FIG. 4 depicts a perspective illustration of the distal end of the distal portion of FIG. 3, with the tip removed for clarity.

The FFR catheter 102 includes shaft 103 including a proximal portion 106 (also referred to as a "proximal shaft portion") and a distal portion 108 (also referred to as a "distal shaft portion"). A pressure sensor 110, shown in FIG. 1 and in greater detail in FIGS. 2-4, is suspended within a housing 112 of the distal portion 108. The pressure sensor 110 may mounted onto a flexible printed circuit board 114 (hereafter referred to as a "flex PCB" for simplicity). The flex PCB 114 is coupled to the housing 112 within a sensor lumen 116 of the distal portion 108 such that the pressure sensor 110 is suspended within an open seat 122 of the housing 112. The pressure sensor 110 is covered by a cover 118. The cover 118 is a separate component attached to the housing 112 of the distal shaft 108 during manufacture to simplify manufacturing of the distal portion 108 with the pressure sensor 110 suspended therein. As used herein, the term "separate" when used to describe that the cover 118 is a "separate" piece attached to the distal shaft 110 during manufacture, it is meant that the cover 118 is not formed as part of the distal portion 108 of shaft 103. Instead, the two pieces are separate and are attached as described below during manufacture. For example, and not by way of limitation, a distal shaft portion that is formed with a portion covering a pressure sensor would not be a "separate" cover. Similarly, a "cover" that is co-formed with a "distal shaft portion", such as by molding, is not considered a "separate" cover attached to the distal shaft portion.

In the embodiment shown in FIG. 1, the shaft 103 is a multi-lumen extrusion including a guidewire lumen 120 extending through the proximal portion 106 and the distal portion 108. The guidewire lumen 120 is configured to receive a guidewire GW. However, instead of the over-the-wire configuration shown in FIG. 1, the FFR catheter 102 may have a rapid exchange configuration wherein the guidewire lumen 120 extends through the distal portion 108 and a portion of the proximal portion 106, and the guidewire GW exits through a rapid exchange port (not shown) in a distal portion of the proximal portion 106. The FFR catheter 102 also includes the sensor lumen 116 extending through the proximal portion 106 and a proximal portion of the distal portion 108. In an embodiment, the sensor lumen 116 is of a consistent cross-sectional profile along the entire length of the sensor lumen 116. In other embodiments, the sensor lumen 116 may have a larger cross-sectional profile distal of the open seat 122 for simplifying the installation of the flex PCB 114 and the pressure sensor 110 mounted thereon, and a smaller cross-sectional profile proximal of the open seat 122 for receiving only the flex PCB 114. The shaft 103 includes a proximal end 124 coupled to a hub or luer 126. The shaft 103 may be formed of polymeric materials, non-exhaustive examples of which include polyethylene, polyether block amide (PEBA), polycarbonate, acrylonitrile butadiene styrene (ABS), polyether ether ketone (PEEK), polyamide, polyimide, and/or combinations thereof, either blended or co-extruded.

As shown in FIGS. 2-3, the distal portion 108 of shaft 103 includes the housing 112, a distal portion of the flex PCB 114, the pressure sensor 110, the cover 118, a tip 134, and an aperture 136. The shaft 103 includes a distal end 132 at a distal end of the distal portion 108. A distal portion of the guidewire lumen 120 extends through the distal portion 108. A distal portion of the sensor lumen 116 extends through the housing 112 of the distal portion 108. The distal portion 108 is configured for measuring a pressure distal of a stenosis. More specifically, the distal portion 108 is configured such that the pressure sensor 110 and the tip 134 are disposed on the distal side DS of the stenosis ST such that the pressure sensor 110 can measure a distal pressure $P_d$ distal of the stenosis ST, as shown in FIG. 1.

In the embodiment of FIGS. 1-4, the housing 112 of the distal portion 108 is of a generally tubular shape having a proximal end and a distal end 140, as shown in FIGS. 3 and 4. The housing 112 defines the open seat 122, extending from an outer surface 156 of the housing 112 inward. The open seat 122 is configured to receive the pressure sensor 110 and a portion of the flex PCB 114 and is sized to allow for movement of the pressure sensor 110 suspended therein. The open seat 122 is further configured to receive a fluid therein from the aperture 136. The housing 112 further defines a through-hole 142, extending from the outer surface 156 of the housing 112 inward to the sensor lumen 116. The through-hole 142 is configured to provide access to the sensor lumen 116 to aid in the coupling of the flex PCB 114 to the housing 112 within the sensor lumen 116.

While the proximal portion 106 and the distal portion 108 of the shaft 103 of the FFR catheter 102 are described herein as a single extrusion, this is not meant to be limiting, and in another embodiment, the proximal portion 106 and the distal portion 108 may be separate components with a proximal end of the distal portion 108 coupled to a distal end of the proximal portion 106. If formed as separate components, the distal portion 108 may be coupled to the proximal portion 106 by methods such as, but not limited to adhesives, fusing, welding, or any other method suitable for the purposes described herein In the embodiment of FIGS. 3 and 4, the open seat 122 is shown as a generally rectangular cuboid. However, this is not meant to be limiting. The open seat 122 may be of any shape suitable to house the pressure sensor 110 and the flex PCB 114 onto which the pressure sensor 110 is mounted and provide sufficient space for fluid to enter the open seat 122 such that the pressure sensor 110 may measure a pressure of the fluid. The open seat 122 may be formed in the housing 112 of the distal portion 108 by various methods, non-limiting examples of which include the open seat 122 formed as part of a molding process, a skiving process, machining, laser ablation, punching, or other suitable methods.

Although shown in FIGS. 3 and 4 with one (1) through-hole 142 positioned proximal of the open seat 122, in alternative embodiments, more than one (1) through-hole 142 may be utilized with the housing 112 and positioned proximal and/or distal of the open seat 122 in any combination. Even further, while the through-hole 142 is shown as a generally circular aperture, this is not meant to be limiting and the through-hole 142 may be of any shape suitable to provide access to the sensor lumen 116 for the purposes described herein. The through-hole 142 may be formed in the housing 112 by various methods, non-limiting examples of which include a skiving process, machining, laser-etching, punching, or other suitable methods.

Figure 5:
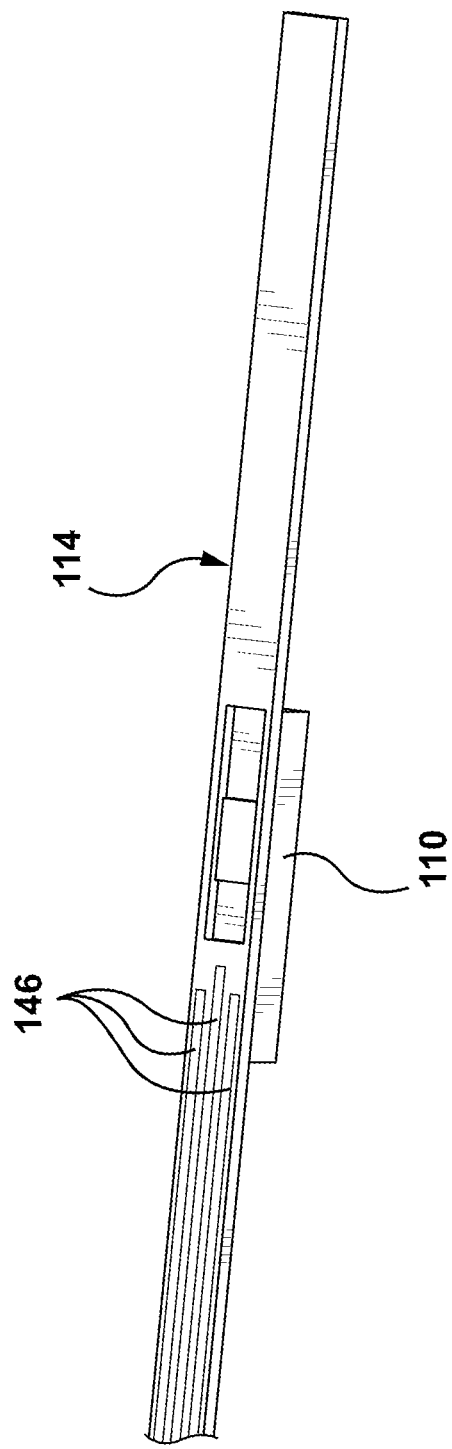
FIG. 5 depicts a perspective view of a flex PCB with a mounted pressure sensor.

In an embodiment shown in greater detail in FIG. 5, the flex PCB 114 is a flexible printed circuit board including the sensor traces 146 laminated between layers of polymer such as, but not limited to polyethylene terephthalate (PET), polyimide, and adhesive sandwich. The pressure sensor traces 146 may be formed of suitable materials such as, but not limited to copper. Alternatively, the flex PCB 114 may be formed by photolithography. The flex PCB 114 is configured to be coupled to the housing 112 of the distal portion to suspend the pressure sensor 110 within the open seat 122 of the distal portion 108 of shaft 103, as best shown in FIGS. 3 and 4. The flex PCB 114 is sized to be received within the sensor lumen 116. With the flex PCB 114 disposed within the sensor lumen 116 and coupled to the distal portion 108, the pressure sensor 110 is suspended within the open seat 122 by the flex PCB 114 and is isolated from both external stresses on the FFR catheter 102 and from stresses emanating from the pressure sensor 110, itself. More specifically the pressure sensor 110 is isolated from external stresses on the distal portion 108 generated by advancement through and positioning within the often tortuous vasculature. Thus, stresses imparted on the distal portion 108 are not transmitted to the pressure sensor 110 and the sensor readings of the pressure sensor 110 are not affected by the stress loads on the distal portion 108 of the FFR catheter 102. The flex PCB 114 is coupled to the housing 112 of the distal portion 108 at a proximal fixation point 148 proximal of the open seat 122 and a distal fixation point 150 distal of the open seat 122. While described as having two (2) fixation points 148, 150, this is not meant to be limiting, and the flex PCB 114 may be coupled to the housing 112 at more or fewer fixation points either proximal or distal of the open seat 122, in any combination. The flex PCB 114 may be coupled to the housing 112 within the sensor lumen 116 by methods such as, but not limited to adhesives, a mechanical interlock, thermal reflow, or other suitable methods.

The pressure sensor 110 includes a pressure-sensing surface 144, as best shown in FIG. 3. The pressure sensor 110 may be a piezo-resistive pressure sensor, a piezo-electric pressure sensor, a capacitive pressure sensor, an electromagnetic pressure sensor, an optical pressure sensor, and/or combinations thereof suitable for the purpose described herein. While the pressure sensor 110 is shown in FIG. 3 configured with the pressure-sensing surface 144 facing radially outward, the pressure-sensing surface 144 may face in other directions to measure distal pressure $P_d$ of a fluid outside the distal portion 108 that has entered the open seat 122 through the aperture 136. The pressure sensor 110 is further configured to communicate a measured distal pressure $P_d$ with the processing device 104 through sensor traces 146 of the flex PCB 114, shown in FIG. 3. The sensor traces 146 form a wired connection similar to the wired connection as described in U.S. Patent Application Publication No. 2015/0305633 A1 to McCaffrey et al., incorporated by reference herein in its entirety. The pressure sensor 110 is coupled to the flex PCB 114 and suspended within the open seat 122 of the distal portion 108. The pressure sensor 110 may be coupled to the flex PCB 114, for example, and not by way of limitation, by adhesives, fusing, welding, or any other method suitable for the purposes of the present disclosure. The pressure sensor 110 is further coupled to the sensor traces 146 of the flex PCB 114. The pressure sensor 110 may be coupled to the sensor traces 146 for example, and not by way of limitation, by soldering, fusing, welding, for any other method suitable for the purposes of the present disclosure. While shown with three (3) sensor traces 146, this is not meant to be limiting, and the flex PCB 114 may include more or fewer sensor traces 146.

In an embodiment, the tip 134 is of a generally frusto-conical shape. The tip 134 includes the proximal end 152 coupled to the distal end 140 of the housing 112, and a distal end 154, as best shown in FIG. 3. The tip 134 may be formed of polymeric materials, non-exhaustive examples of which include polyethylene, polyether block amide (PEBA), polycarbonate, acrylonitrile butadiene styrene (ABS), polyether ether ketone (PEEK), polyamide and/or combinations thereof, or other materials suitable for the purposes described herein.

Figure 6:
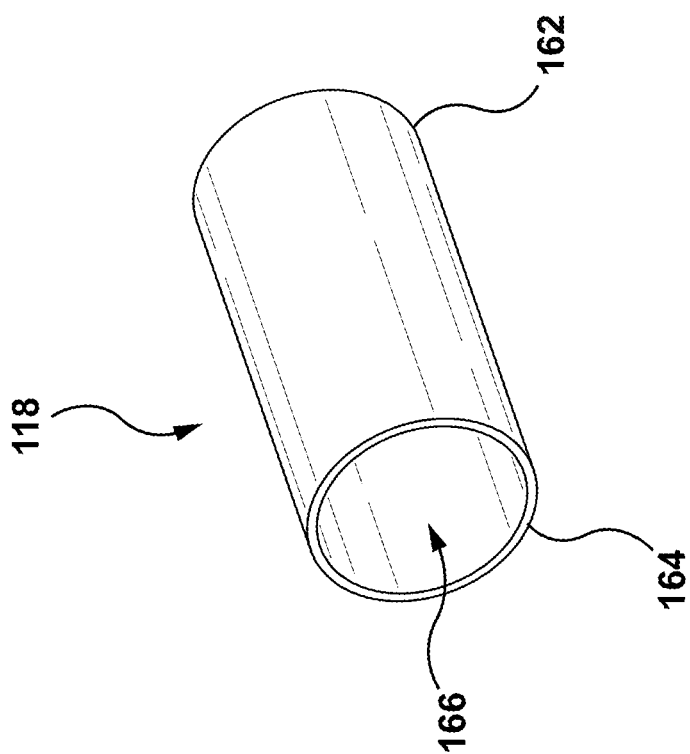
FIG. 6 depicts a perspective view of the cover of the catheter of FIG. 1.
Figure 7:
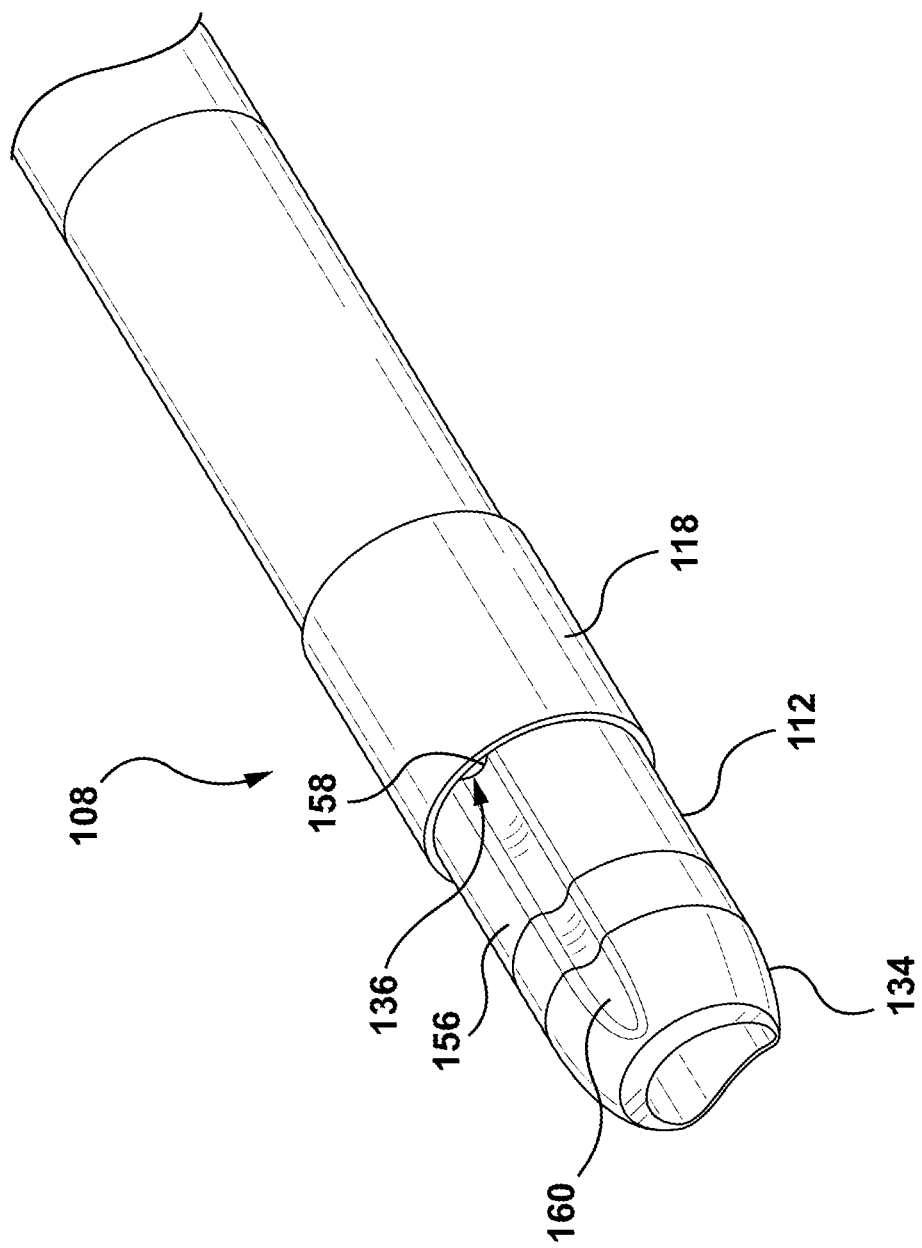
FIG. 7 depicts a perspective illustration of the distal portion of the catheter of FIG. 1, with the cover in a first configuration.

In an embodiment, the cover 118 is of a generally tubular shape with a proximal end 162, a distal end 164, and a cover lumen 166, as shown in FIG. 6. The cover lumen 166 extends through the cover 118 between the proximal end 162 and the distal end 164. The cover 118 may be disposed in a second configuration, as shown in FIG. 3, wherein the cover 118 is not coupled to the housing 112 and is disposed proximal of the open seat 122. The second configuration is used during manufacture to simplify installation of the flex PCB 114 and the pressure sensor 110. The cover 118 is moved during manufacture to a first configuration shown in FIG. 7, wherein the cover 118 is coupled to the housing 112 such that a portion of the housing 112, the open seat 122 (obscured by the cover 118 in FIG. 7), and the pressure sensor 110 (obscured by the cover 118 in FIG. 7) are disposed within the cover lumen 166. The cover 118 is configured to protect the pressure sensor 110 when the cover 118 is in the first configuration. The cover 118 may be coupled to the housing 112 by various methods, including, but not limited to adhesives, heat shrink tubing, swage coupling, interference fit, mechanical interlock, or other suitable methods. The cover 118 may be formed of various materials, non-limiting examples including stainless steel, gold, platinum, and/or iridium, and alloys thereof. In some embodiments, the cover may be formed of or include radiopaque materials (e.g., gold, platinum, and/or iridium) such that the cover 118 may act as a marker band. While described as a tube or cylinder, the cover 118 may include alternative shapes such as, but not limited to a half-cylinder.

As noted above, the aperture 136 is in fluid communication with the open seat 122, as shown in FIGS. 2, 3, and 4. The aperture 136 is an opening extending from the outer surface 156 of the housing 112 and extending into the open seat 122 of the distal portion 108. The aperture 136 is configured to allow fluid therethrough to the pressure sensor 110. More specifically, the aperture 136 is configured to enable fluid flow from outside the housing 112 through the aperture 136 and into the open seat 122, and into contact with the pressure-sensing surface 144 of the pressure sensor 110. In an embodiment shown in FIG. 7, the aperture 136 is formed between an inner surface of the cover 118 and the outer surface 156 of the housing 112 at a distal end 158 of the open seat 122. More precisely, the aperture 136 is formed via a longitudinal groove or depression 160 disposed within a proximal portion of the tip 134 and extending proximally within a distal portion of the housing 112 to the distal end 158 of the open seat 122 (obscured from view in FIG. 7 by the cover 118, but visible in FIG. 3). The longitudinal groove 160 provides fluid flow to the aperture 136, and the aperture 136 provides the fluid flow to the open seat 122 and the pressure sensor 110, suspended therein. The aperture 136 is sized such that a sufficient amount of blood flows into the open seat 122 of the housing 112. In an embodiment, the aperture 136 is in the range of 100 to 500 microns in diameter. aperture 136 may be formed as an integral component of the housing 112 and the tip 134 of the distal portion 108 or may be formed by removing material from the housing 112 and the tip 134 by any suitable method such as, but not limited to heat processes with mandrels and dies, cutting, machining, laser ablation, or other methods suitable for the purposes described herein. The aperture 136 is shown as generally tubular, but this is not meant to limit the design, and other shapes may be utilized. Moreover, while only one (1) aperture 136 is shown, this is not meant to be limiting, and more than one (1) aperture 136 may be utilized, and disposed at other locations of the distal portion 108.

With an understanding of the components above, it is now possible to describe their interaction as a system to provide stable, accurate distal pressure measurements for accurate FFR calculations by reducing torsional forces transmitted to the pressure sensor 110 from the shaft 103, and in particular the distal portion 108 of the shaft 103.

Figure 8:
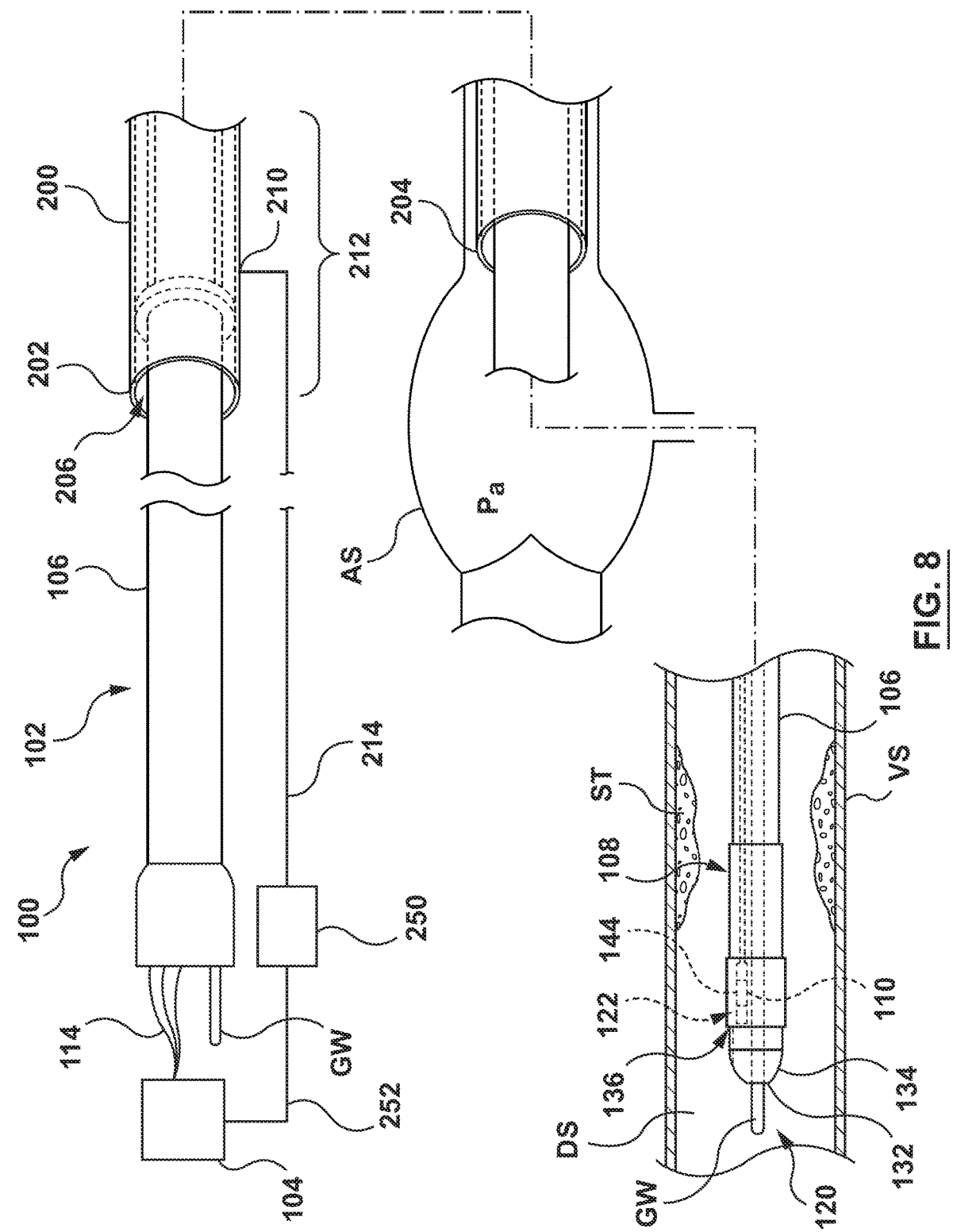
FIG. 8 depicts a schematic view of the system of FIG. 1 used to calculate Fractional Flow Reserve.

Referring to FIG. 8, the system 100 is shown disposed through a guide catheter 200, which is utilized as the proximal pressure-sensing device, as explained below. The guide catheter 200 and the guidewire GW are advanced through the vasculature to a desired site. The guidewire GW may be back-loaded into the FFR catheter 102 (i.e., the proximal end of the guidewire GW is loaded into the distal end of guidewire lumen 120 at the distal end 132 of the shaft 103. The FFR catheter 102 may then be advanced over the guidewire GW and through a lumen 206 of the guide catheter 200 to the desired treatment site. In particular, with a distal end 204 of the guide catheter 200 disposed at a desired site proximal of the stenosis ST, such as in the aortic sinus AS, the FFR catheter 102 is advanced through the lumen 206 and distal of the distal end 204 of the guide catheter 200. The FFR catheter 102 is advanced such that the housing 112 with the pressure sensor 110 disposed therein is disposed distal of the stenosis ST of the vessel VS. Blood flow from the aortic sinus AS fills the lumen 206 and tubing 214 via a port 210 of a proximal portion 212 of the guide catheter 200. The blood pressure $P_a$ at the distal end 204 of the guide catheter 200 is measured by an external pressure transducer 250 via the fluid (blood) column extending through the lumen 206 and the tubing 214. Thus, the external pressure transducer 250 is configured to measure proximal, or aortic (AO) pressure $P_a$ at the distal end 204 of the guide catheter 200.

The external pressure transducer 250 is configured to communicate the measured proximal pressure $P_a$ to the processing device 104 via a pressure transducer wire 252, as shown in FIG. 8. While the pressure transducer 250 is shown in FIG. 8 as communicating the measured proximal pressure $P_a$ with the processing device 104 via the pressure transducer wire 252, this is not meant to limit the design and the pressure transducer 250 may communicate with the processing device 104 by any means suitable for the purposes described, including, but not limited to, electrical cables, optical cables, or wireless devices.

Simultaneously, blood on the distal side DS of the stenosis ST flows through the aperture 136 and into the open seat 122. The blood within the open seat 122 is in contact with the pressure-sensing surface 144 of the pressure sensor 110, suspended therein. The pressure of the blood within the open seat 122 is equal to the pressure on the distal side DS of the stenosis ST.

The suspension of the pressure sensor 110 within the open seat 122 isolates the pressure sensor 110 from torsional forces on the shaft 103, in particular the distal portion 108 thereof, that are transferred to a directly mounted pressure sensor. As used herein, the term "directly mounted" is meant to indicate that a portion of the pressure sensor is in contact with the shaft, and that stresses imparted on the shaft are transmitted to the pressure sensor and deflect the diaphragm of the pressure sensor. The deflected diaphragm of the pressure sensor may result in sporadic and inaccurate pressure measurement. Thus, the suspended pressure sensor 110 provides a stable and accurate measured distal pressure $P_d$ as the pressure sensor 110 is not affected by stresses on the distal portion 108 of the shaft 103. The measured distal pressure $P_d$ sensed by the pressure sensor 110 is communicated to processing device 104. The processing device 104 calculates the Fractional Flow Reserve (FFR) based on the measured distal pressure $P_d$ divided by the measured proximal/aortic pressure $P_a$, or FFR=$P_d/P_a$.

Figure 9:
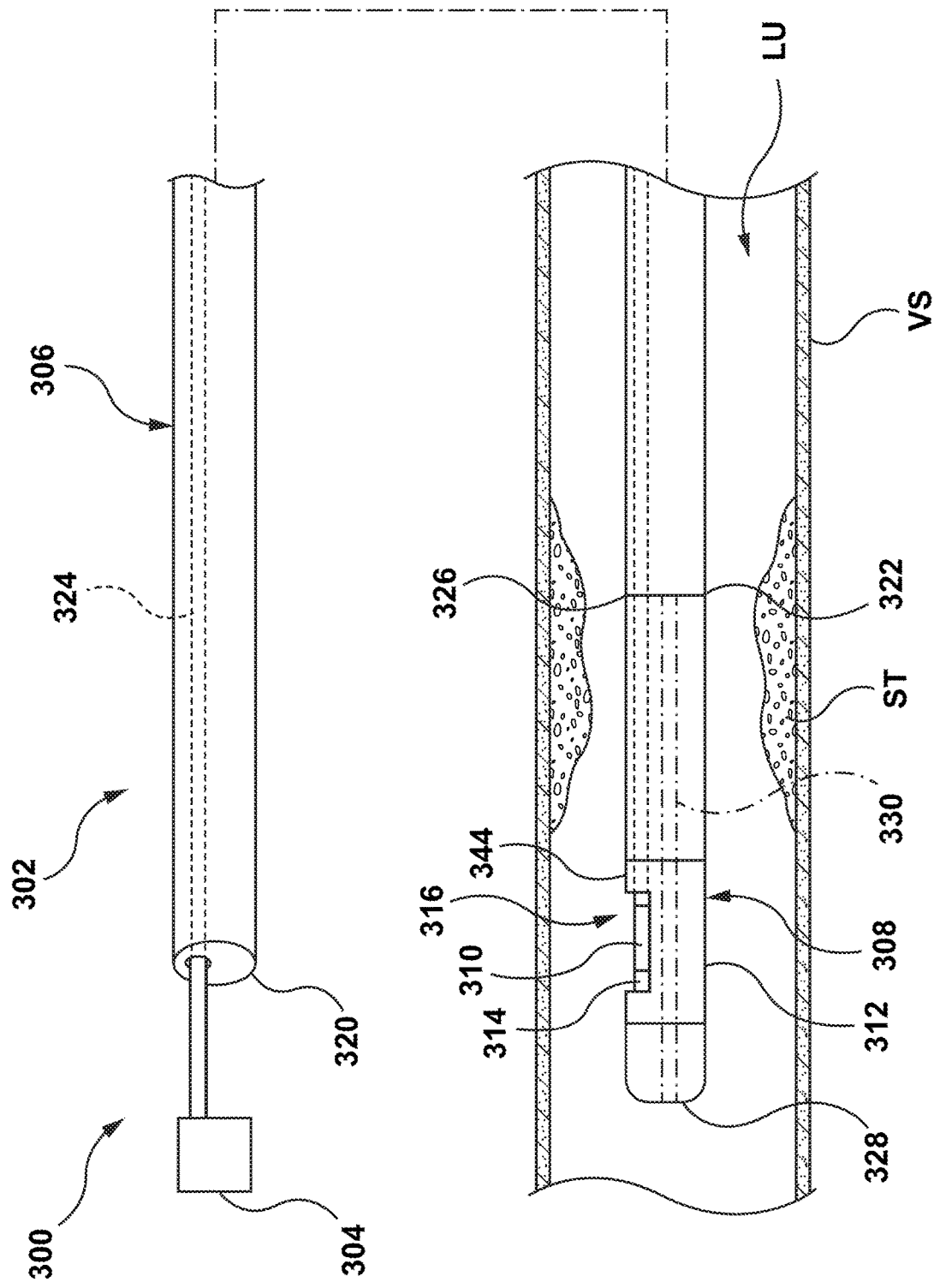
FIG. 9 depicts a partial side and perspective view of a guidewire for measuring a distal pressure in accordance with another embodiment hereof.

FIG. 9 is a schematic partial side and partial perspective illustration of a system 300 for calculating a Fractional Flow Reserve (FFR) according to another embodiment hereof. The system 300 includes an FFR guidewire 302, a proximal pressure-sensing device (not shown), and a processing device 304. The FFR guidewire 302 is configured to be disposed with a proximal portion thereof extending outside of a patient and a distal portion thereof positioned in situ within a lumen LU of a vessel VS having a stenosis ST. In an embodiment, the vessel VS is a blood vessel such as but not limited to a coronary artery.

Figure 10:
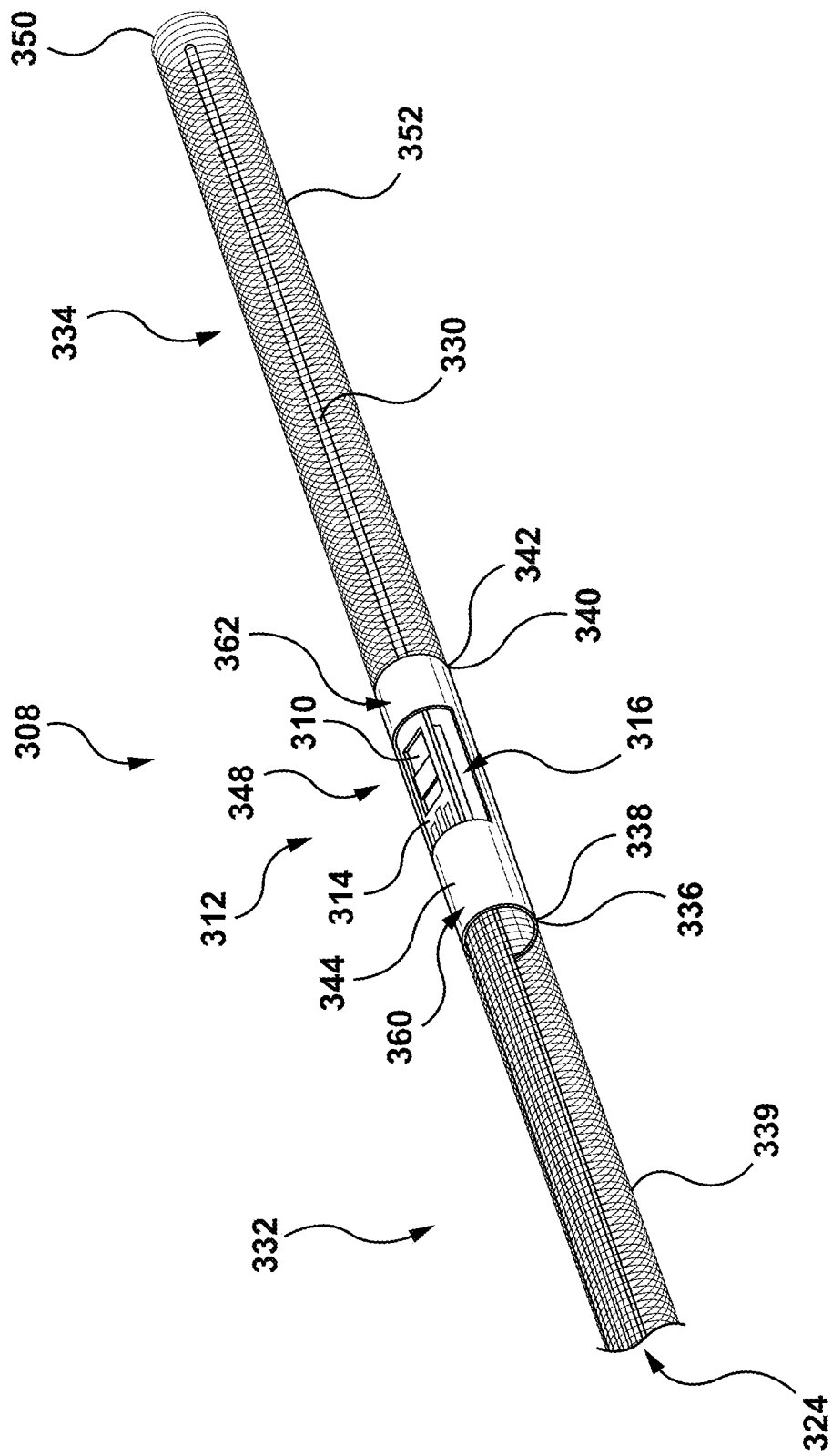
FIG. 10 depicts a perspective illustration of a distal portion of the guidewire of FIG. 9 in accordance with an embodiment hereof.

The FFR guidewire 302 includes a proximal portion 306 and a distal portion 308. A pressure sensor 310, shown in FIG. 9 and in greater detail in FIG. 10, is disposed within a housing segment 312 of the distal portion 308. The pressure sensor 310 is mounted onto a flexible printed circuit board 314 (hereafter referred to as a "flex PCB" for simplicity), and the flex PCB 314 is coupled to a housing 344 of the housing segment 312 within an open seat 316. The pressure sensor 310 suspended within the open seat 316 of the housing 344. The proximal portion 306 of the FFR guidewire 302 includes a proximal end 320 and a distal end 322. The proximal portion 306 may be a generally tubular shaped hypotube configured to have sufficient pushability to advance the FFR guidewire 302 through the tortuous vasculature to a desired treatment site. A proximal portion of a sensor lumen 324 extends from the proximal end 320 to the distal end 322 within the proximal portion 306.

In the embodiment shown in FIG. 9, the distal portion 308 includes a proximal end 326 coupled to the distal end 322 of the proximal portion 306, and a distal end 328. An inner wire 330 extends from the proximal end 326 to the distal end 328 of the distal portion 308. The distal portion 308 further includes the housing segment 312 disposed between a proximal segment 332 and a distal segment 334 of the distal portion 308, as best viewed in FIG. 10. A distal end 336 of the proximal segment 332 is coupled to a proximal end 338 of the housing segment 312, and a distal end 340 of the housing segment 312 is coupled to a proximal end 342 of the distal segment 334. The distal portion 308 of the FFR guidewire 302 further includes a distal portion of the sensor lumen 324 extending through the proximal segment 332 and a portion of the housing segment 312 of the distal portion 308. The sensor lumen 324 is configured to receive the flex PCB 314. In an embodiment, the sensor lumen 324 is of a consistent cross-sectional profile along the entire length of the sensor lumen 324. In other embodiments, the sensor lumen 324 may have a larger cross-sectional profile within the housing segment 312 for simplifying installation of the flex PCB 314 and the pressure sensor 310, and a smaller cross-sectional profile proximal of the housing segment 312 for receiving only the flex PCB 314.

In the embodiment shown in FIG. 10, the proximal segment 332 of the distal portion 308 includes a helically wound outer wire 339, a proximal portion of the inner wire 330, a proximal end 343 (not visible in FIG. 10), the distal end 336, and a corresponding portion of the sensor lumen 324. The corresponding portion of the sensor lumen 324 extends from the proximal end 343 to the distal end 336 of the proximal segment.

In the embodiment of FIG. 10, the housing segment 312 includes the proximal end 338, the distal end 340, the housing 344, and a corresponding portion of the inner wire 330 (obscured by the pressure sensor 310, the flex PCB 314, and the sensor lumen 324 in FIG. 10). The housing segment 312 further includes a corresponding portion of the sensor lumen 324. The housing segment 312 is configured to provide a platform to mount the flex PCB 314 to suspend the pressure sensor 310, which is coupled to the flex PCB 314, within the open seat 316. The pressure sensor 310 is thereby isolated from external stresses on the FFR guidewire, and in particular the distal portion 308 thereof, as described previously with respect to the suspended pressure sensor 110 and the distal portion 108 of FIGS. 1-8. The housing 344 of the housing segment 312 of the distal portion 308 is of a generally tubular shape. The housing 344 defines the open seat 316, extending from an outer surface of the housing 344 inward. The open seat 316 is configured to receive the suspended pressure sensor 310 and a portion of the flex PCB 314 therein. The open seat 316 is further configured to receive a fluid therein from an aperture 348. The open seat 316 may be formed as an integral component of the housing 344 or may be formed by removing material from the housing 344 by any suitable method such as, but not limited to heat process with mandrels and dies, cutting, machining, or other methods suitable for the purposes described herein. The housing 344 may be formed of various materials, non-limiting example of which include metals, metal alloys, polymers, composites, or other suitable materials.

As shown in the embodiment of FIG. 10, the distal segment 334 of the distal portion 308 includes the proximal end 342, a distal end 350, a helically wound outer wire 352, and a distal portion of the inner wire 330.

The proximal, distal, and housing segments 332, 334, 312 may each include structures to vary the level of stiffness, flexibility, and torquability of each segment. Thus, the flexibility of each segment may be different than the other segments. Further, the flexibility of each segment may vary along its length. For example, the distal segment 334 may have a greater flexibility at the distal end 350 than at the proximal end 342 to enhance atraumatic advancement of the FFR guidewire 302 thorough the tortuous vasculature. In another example, the housing segment 312 may have increased stiffness to support the flex PCB 314 and the pressure sensor 310 suspended therein. In an example, the distal segment 334 may be 3 centimeters (cm) in length, the housing segment 312 may be between 0.3 centimeter (CM) and 1.5 centimeters (cm) inclusive, and the proximal segment 332 may be 30 centimeters (cm). The overall length of the FFR guidewire 302 may be in the range of 170 cm for a rapid exchange configuration and 300 cm for an over the wire configuration.

Components of the proximal, housing, and distal segments 332, 312, 334 may be formed of various materials including, but not limited to metals, metal alloys, polymers, composites, or other suitable materials. The proximal, housing, and distal segments 332, 312, 334 may be coupled to the adjacent segment by various methods, non-limited examples of which include adhesives, fusing, welding, mechanical couplers, or other suitable methods. The proximal segment 332 of the distal portion 308 may be coupled to the proximal portion 306 by methods such as, but not limited to adhesives, fusing, welding, mechanical couplers, or other suitable methods.

The flex PCB 314 is similar to the flex PCB 114 described with the embodiment of FIG. 1. Consequently, the details and alternatives of the flex PCB 314 will not be repeated. The flex PCB 314 is coupled to the housing 344 at a proximal fixation point 360 proximal of the open seat 316 and a distal fixation point 362 distal of the open seat 316. While described as having two (2) fixation points 360, 362, it will be understood that the flex PCB 314 may be coupled to the housing 344 at more or fewer fixation points either proximal or distal of the open seat 316, in any combination. The flex PCB 314 may be coupled to the housing 344 by methods such as, but not limited to adhesives, or other suitable methods.

The pressure sensor 310 is similar to the pressure sensor 110 described previously. Therefore, details of the pressure sensor 310 will not be repeated here.

As noted above, the housing 344 includes the aperture 348 in fluid communication with the open seat 316. The aperture 348 is an opening extending from an outer surface of the housing 344 into the open seat 316. The aperture 348 is configured to enable fluid flow therethrough. Thus, fluid outside the housing segment 312 may flow through the aperture 348, into the open seat 316, and into contact with the pressure-sensing surface 340 of the pressure sensor 310. While the aperture 348 is shown with a specific shape, this is not meant to be limiting, and the aperture 348 may have other shapes and sizes such that a sufficient amount of blood flows into the open seat 316. The aperture 348 may be formed as an integral component of the housing 344 or may be formed by removing material from the housing 344 by any suitable method such as, but not limited to heat process with mandrels and dies, cutting, machining, or other methods suitable for the purposes described herein.

Figure 11:
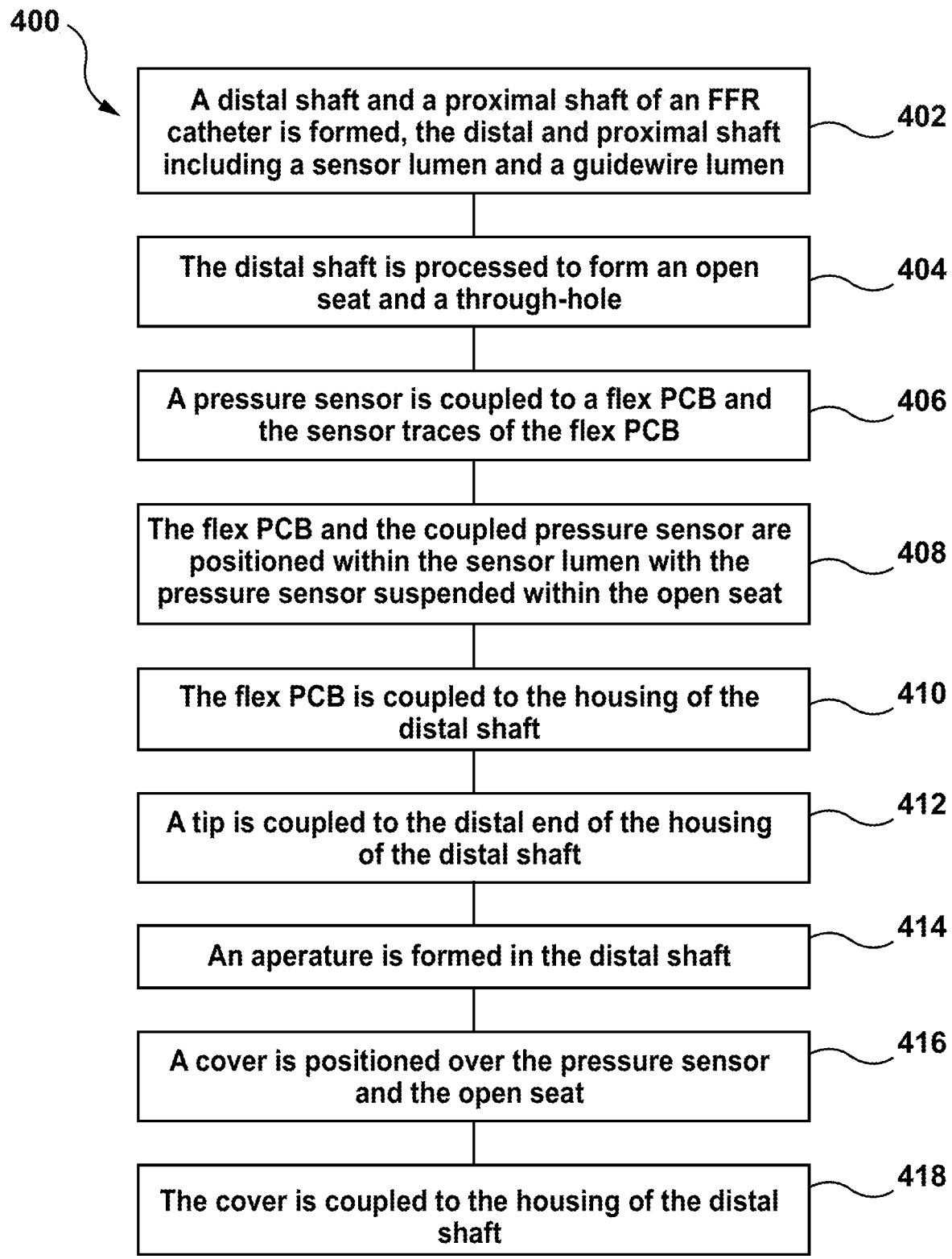
FIG. 11 depicts a block diagram of a method of manufacture of the FFR catheter of FIG. 1 according to an embodiment hereof.

Referring to FIG. 11, a method 400 of manufacturing a distal portion 108 of an FFR catheter 102 with a suspended pressure sensor 110 for measuring a distal pressure according to an embodiment hereof is described.

In step 402, the shaft 103, including the distal portion 108, the proximal portion 106, the guidewire lumen 120, and the sensor lumen 116, is formed by an extrusion process. In step 404, the distal portion 108 of the shaft 103 is processed to form the open seat 122 and the through-hole 142.

Figure 12:
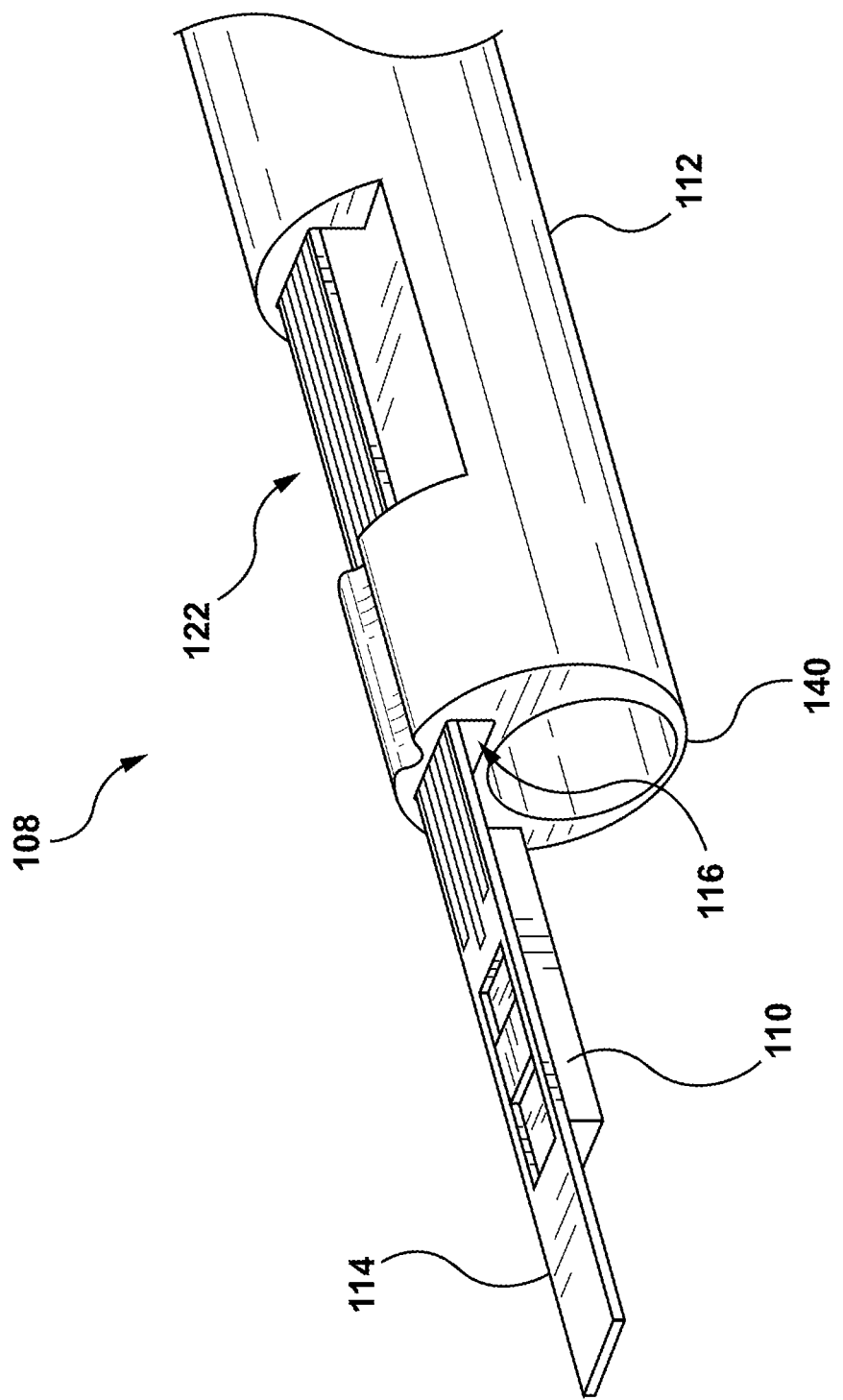
FIG. 12 depicts a perspective view of a distal portion of the catheter of FIG. 1 with the pressure sensor mounted on the flex PCB and the flex PCB extending distally of the housing, in accordance with a step of the method of FIG. 11.
Figure 13:
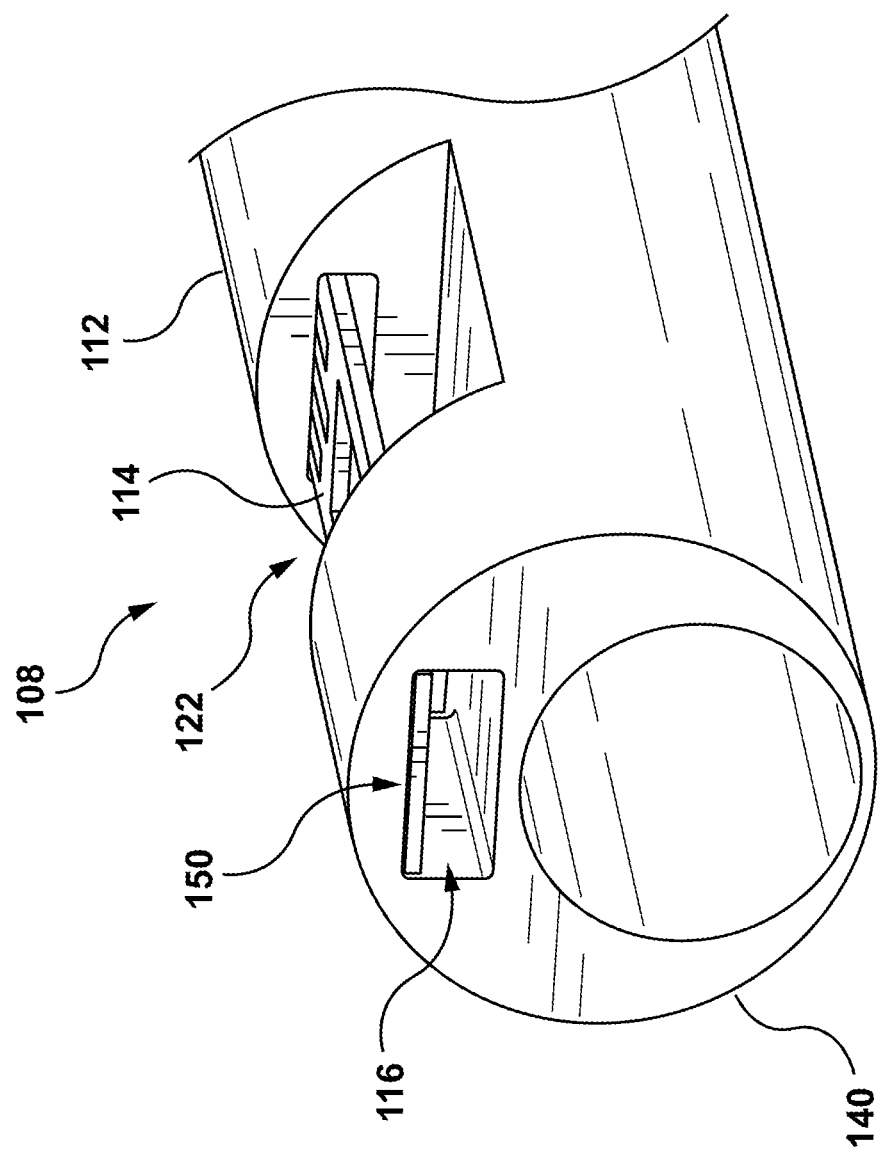
FIG. 13 depicts a perspective view of the housing of the catheter of FIG. 1 with the pressure sensor in the open seat of the housing, in accordance with a step of the method of FIG. 11.

In step 406, the pressure sensor 110 is coupled to the flex PCB 114 and the sensor traces 146 of the flex PCB 114. In step 408, the flex PCB 114 is threaded through the sensor lumen 116 of the shaft 103. In one embodiment, the flex PCB 114 is threaded through the sensor lumen 116 without the sensor mounted on the flex PCB 114. A distal portion of the flex PCB 114 extends distally beyond a distal end of the housing 112, as shown in FIG. 12. The pressure sensor 110 may then be mounted on the flex PCB 114. Next, the flex PCB 114 with the sensor 110 mounted thereon may be moved proximally through the portion of the sensor lumen 116 distal of the open seat 122 until the pressure sensor 110 is disposed within the open seat 122 (as shown in FIG. 4). In another embodiment, the pressure sensor 100 may be coupled to the flex PCB 114 prior to threading the flex PCB 114 through the sensor lumen 116. In such an embodiment, after the sensor 110 is coupled to the flex PCB 114, a proximal end of the flex PCB 114 is inserted into a distal end of the sensor lumen 116, and the flex PCB 114 is advanced proximally until the sensor 110 is adjacent the distal end 140 of the housing 112, as shown in FIG. 12. Next, the flex PCB 114 with the sensor 110 mounted thereon may be moved proximally through the portion of the sensor lumen 116 distal of the open seat 122 until the pressure sensor 110 is disposed within the open seat 122 (as shown in FIG. 13).

Figure 14:
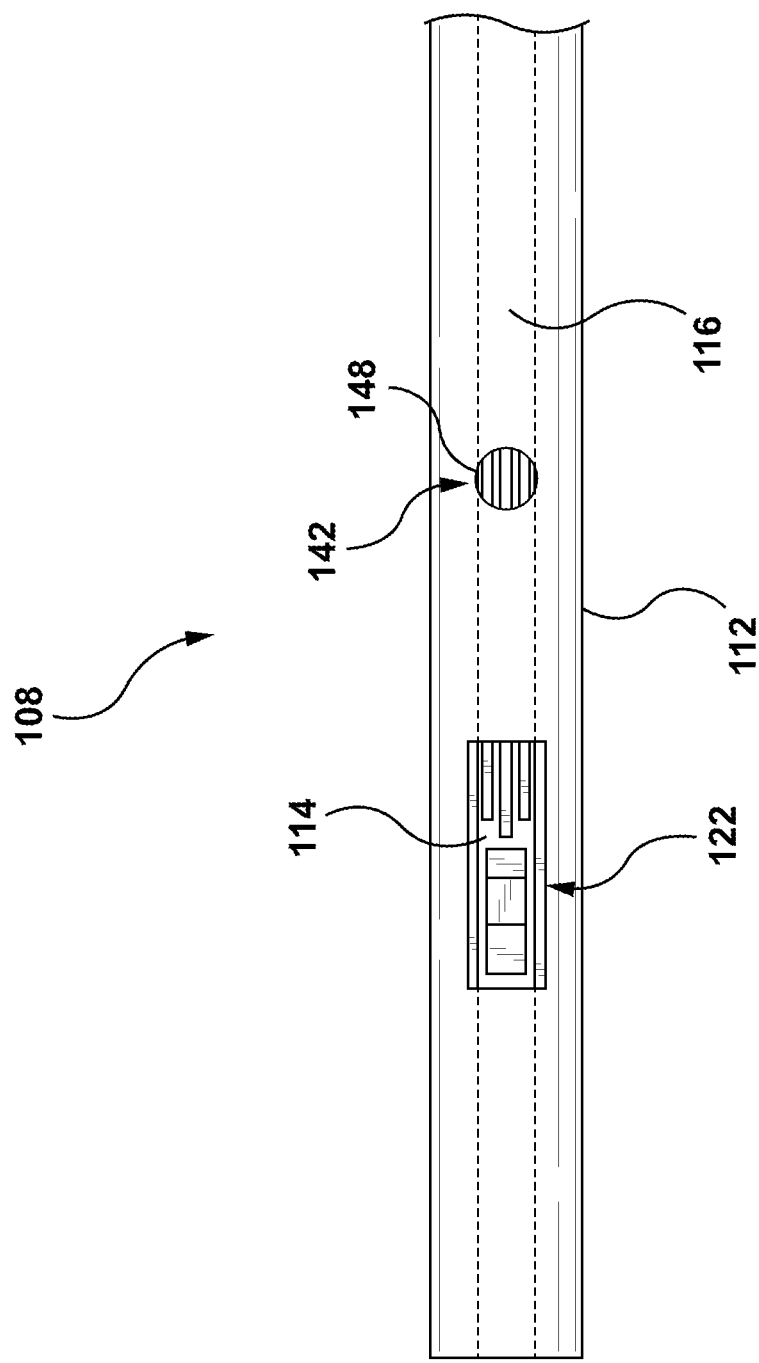
FIG. 14 depicts a top view of the distal portion of the catheter of FIG. 1 showing a through hole and a proximal fixation point to illustrate a step of the method of FIG. 11.

Next, in step 410, the flex PCB 114 is coupled to the housing 112 of the distal portion 108. More precisely, the flex PCB 114 is coupled at the proximal fixation point 148 to an inner surface of the housing 112 within the sensor lumen 116, proximal of the open seat 122. Access to the proximal fixation point 148 is available via the through-hole 142, as shown in FIG. 14. Further, the flex PCB 114 is coupled at the distal fixation point 150 to the inner surface of the housing 112 within the sensor lumen 116, distal of the open seat 122. Access to the distal fixation point 150 is available via the sensor lumen 116 at the distal end 140 of the housing 112, as shown in FIG. 13.

In step 412, the tip 134 is coupled to the distal end 140 of the housing 112 in a step 412.

In step 414, the aperture 136 is created by processing the housing 112 and the tip 134 of the distal portion 108 to form the longitudinal groove 160.

Figure 15:
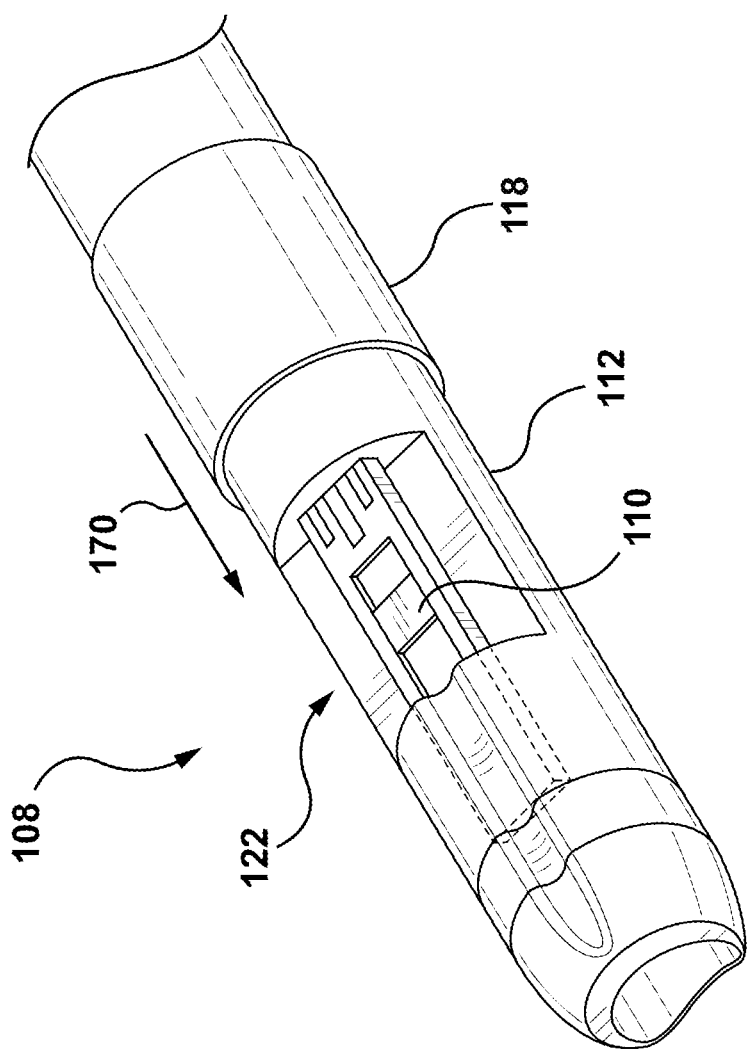
FIG. 15 depicts a perspective view of the housing of the catheter of FIG. 1 showing a cover being positioned over the open seat and the pressure sensor, in accordance with a step of the method of FIG. 11.

In step 416, the cover 118 is positioned over the open seat 122 of the housing 112 with the pressure sensor 110 suspended therein by distally sliding or translating the cover 118 in a direction indicated by arrow 170 over the housing 112 of the distal portion 108, as shown in FIG. 15.

In a next step 418, the cover 118 is coupled to the housing 118 or the distal portion 108.

Although the method describes a particular order of the steps of the method of FIG. 11, the order may be different. For example, and not by way of limitation, the aperture 136 may be formed at any time. Further, while the method describes creating the aperture 136 via the formation of the longitudinal groove 160 in both the tip 134 and the housing 112, this is not meant to limit the method, and step 414 may alternatively include creating the aperture 136 in the tip 134, in the housing 112, and/or in the cover 118, in any combination thereof. Even further, more than one aperture 136 may be created.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

What is claimed is:

1. A catheter for measuring a pressure distal of a stenosis, the catheter comprising:
    a shaft including a housing in a distal portion of the shaft;
    a flexible printed circuit board coupled to the housing, wherein a first portion of the flexible printed circuit board is coupled to a distal end of the housing, a second portion of the flexible printed circuit board is coupled to a proximal end of the housing, and a third portion of the flexible printed circuit board is suspended in the housing between the first portion and the second portion;
    a pressure sensor mounted on the third portion of the flexible printed circuit board and suspended within the housing; and
    an aperture configured to allow blood flow into the housing and into contact with the pressure sensor.

2. The catheter of claim 1, wherein the flexible printed circuit board is coupled to the housing at a plurality of fixation points.

3. The catheter of claim 1, further comprising a cover coupled to the housing, the cover including a first configuration wherein the cover covers the pressure sensor.

4. The catheter of claim 3, wherein the aperture is formed between an inner surface of the cover and an outer surface of the housing.

5. The catheter of claim 1, further comprising:
    a sensor lumen extending through the shaft, wherein the flexible printed circuit board is disposed in the sensor lumen; and
    at least one through-hole extending radially through the distal portion of the shaft to the sensor lumen, wherein the at least one through-hole is configured to enable access to couple the flexible printed circuit board to the housing.

6. The catheter of claim 1, wherein the housing includes a guidewire lumen.

7. The catheter of claim 1, wherein the housing includes an open seat, wherein the pressure sensor is suspended within the open seat.

8. The catheter of claim 1, further comprising a sensor lumen extending through the shaft, wherein the sensor lumen includes a first portion proximal of the housing and a second portion distal of the housing, wherein the first portion of the flexible printed circuit board is disposed in the first portion of the sensor lumen and the second portion of the flexible printed circuit board is disposed in the second portion of the sensor lumen.

9. A catheter for measuring a pressure distal of a stenosis, the catheter comprising:

a shaft including a housing in a distal portion of the shaft, the housing including an open seat;

a flexible printed circuit board coupled to the housing;

a pressure sensor coupled to the flexible printed circuit board and suspended within the housing;

an aperture configured to allow blood flow into the housing and into contact with the pressure sensor; and a sensor lumen extending through the shaft, wherein the sensor lumen includes a first portion proximal of the open seat and a second portion distal of the open seat, wherein a first portion of the flexible printed circuit board is disposed in the first portion of the sensor lumen, a second portion of the flexible printed circuit board is disposed in the second portion of the sensor lumen, and a third portion of the flexible printed circuit board with the sensor coupled thereto is suspended in the open seat between the first and second portions of the sensor lumen.

10. The catheter of claim 9, further comprising a through-hole extending through the housing to the first portion of the sensor lumen.

11. The catheter of claim 9, wherein the second portion of the sensor lumen is sized and shaped to fit the third portion of the flexible printed circuit board with the pressure sensor mounted thereon within the second portion of the sensor lumen.

12. The catheter of claim 9, wherein the flexible printed circuit board is coupled to the housing at a plurality of fixation points.

13. The catheter of claim 9, further comprising a cover coupled to the housing, the cover including a first configuration wherein the cover covers the pressure sensor.

14. The catheter of claim 13, wherein the aperture is formed between an inner surface of the cover and an outer surface of the housing.

15. The catheter of claim 9, wherein the housing includes a guidewire lumen.

* * * * *